(12) United States Patent
Cook et al.

US008802094B2

(10) Patent No.: US 8,802,094 B2
(45) Date of Patent: Aug. 12, 2014

(54) METHOD OF REDUCING PHOSPHATE ABSORPTION BY ADMINISTERING ORALLY AN IGY ANTI-INTESTINAL SODIUM PHOSPHATE COTRANSPORTER TYPE 2B ANTIBODY

(75) Inventors: Mark Cook, Madison, WI (US); Martin Petkovich, Kingston (CA); Christian Helvig, Makham (CA); Erica Hellestad, Madison, WI (US); Keith Crawford, Fitchburg, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1136 days.

(21) Appl. No.: 12/447,385

(22) PCT Filed: Oct. 23, 2007

(86) PCT No.: PCT/US2007/082247
§ 371 (c)(1),
(2), (4) Date: Feb. 19, 2010

(87) PCT Pub. No.: WO2008/051980
PCT Pub. Date: May 2, 2008

(65) Prior Publication Data
US 2010/0166760 A1 Jul. 1, 2010

Related U.S. Application Data

(60) Provisional application No. 60/862,876, filed on Oct. 25, 2006.

(51) Int. Cl.
*A61K 39/395* (2006.01)
(52) U.S. Cl.
USPC ........................................................ 424/139.1
(58) Field of Classification Search
USPC ........................................................ 424/139.1
See application file for complete search history.

(56) References Cited

U.S. PATENT DOCUMENTS

| | | | |
|---|---|---|---|
| 5,080,895 A | 1/1992 | Tokoro | |
| 5,597,815 A * | 1/1997 | Deluca et al. | 514/167 |
| 5,980,881 A | 11/1999 | Mitsuka et al. | |
| 5,985,938 A | 11/1999 | Holmes-Farley et al. | |
| 5,989,584 A | 11/1999 | Cook et al. | |
| 6,180,094 B1 | 1/2001 | Sasaki et al. | |
| 6,213,930 B1 | 4/2001 | Cook | |
| 6,380,374 B1 * | 4/2002 | Cannon et al. | 536/23.5 |
| 6,423,754 B1 | 7/2002 | Holmes-Farley et al. | |
| 2002/0156266 A1 | 10/2002 | Cannon et al. | |
| 2004/0087522 A1 | 5/2004 | Marquardt et al. | |
| 2008/0003263 A1 * | 1/2008 | Sunwoo et al. | 424/439 |

FOREIGN PATENT DOCUMENTS

| | | |
|---|---|---|
| JP | 2000-245488 A | 9/2000 |
| JP | 2001-501622 A | 2/2001 |
| WO | 9505184 | 2/1995 |
| WO | 9519373 A1 | 7/1995 |
| WO | 0203788 A2 | 1/2002 |
| WO | 2008051977 A2 | 5/2008 |
| WO | 2008067084 A2 | 6/2008 |

OTHER PUBLICATIONS

Tenehouse, "Phosphate transport: Molecular basis, regulation and pathophysiology," Journal of Steroid Biochemistry and Molecular Biology, Mar. 2007, vol. 103, No. 3-5, p. 572-577.
Lau K., Phosphate Disorders. Saunders; 1986:398-470.
Delmez, et al., "Hyperphosphatemia: Its consequences and treatment in patients with chronic renal disease," Am. J. Kidney Dis, 1992, 19:303-317.
Cross et al., Miner Electrolyte Metab 1990, 16:115-124.
Walton J, et al., Clin Sci 1979, 56:407-412.
Hu, et al., Miner Electrolyte Metab, 1997, 23:7-12.
Peters, et al., Res Exp Med (Berl), 1988, 188:139-149.
Eto, et al. Drug Metab Pharmacokinet, 2006, 21:217-221.
Knox F, et al., Am. J. Physiol. 1977, 233:F261-F268.
Albaaj F & Hutchinson A, Drugs 2003, 63:577-596.
Block G, et al., J. Am. Soc. Nephrol. 2004, 15:2208-2218.
Block G & Port F, Am. J. Kidney Dis. 2000, 35:1226-1237.
Bouillon et al., Endocrine Reviews 1995, 16:200-257.
Hilfiker H., et al., Proc Natl Acad Sci USA. 1998, 95:14564-14569.
Nakano, et al., Arch Histol Cytol 2001, 64:483-491.
Atuma, et al., Am J Physiol Gastrointest Liver Physiol 2001, 280:922.
M. Mantle and Al Allen, 1989, Gastrointestinal mucus, pp. 202-229 in Gastrointestinal Secretions, J.S. Davidson, ed., Butterworth and Co., Great Britain.
Kostelny, et al., "Formation of a bispecific antibody by the use of leucine zippers," J. Immunol. 1992, 148:1547-1553.
Pack and Pluckthun, "Miniantibodies: use of amphipathic helixes to produce functional, flexibly linked dimeric FV fragments with high avidity in *Escherichia coli*," Biochemistry 1992, 31:1579-1584.
Zhu, et al., "Remodeling Domain Interfaces to Enhance Heterodimer Formation," Protein Sci 1997, 6:781-788.
Hu, et al., "Minibody: A Novel Engineered Anti-Carcinoembryonic Antigen Antibody Fragment (Single-Chain Fv-CH3) Which Exhibits Rapid, High-Level Targeting of Xenografts," Cancer Res. 1996, 56:3055-3061.
Adams et al., "Highly Specific in Vivo Tumor Targeting by Monovalent and Divalent Forms of 741F8 Anti-c-erbB-2 Single-Chain Fv," Cancer Res 1993, 53:4026-4034.
McCartney, et al., "Engineering disulfide-linked single-chain Fv dimers [(sFv')2] with improved solution and targeting properties: anti-digoxin 26-10 (sFv')2 and anti-c-erbB-2 741F8 (sFv')2 made by protein folding and bonded through C-terminal cysteinyl peptides," Protein Eng. 1995, 8:301-314.
Biehl, et al. "1-alpha-Hydroxycholecalciferol does not increase the specific activity of intestinal phytase but does improve phosphorus utilization in both cecectomized and sham-operated chicks fed cholecalciferol-adequate diets" Journal of Nutrition, vol. 127, No. 10, 1997, pp. 2054-2059.

(Continued)

*Primary Examiner* — Prema Mertz
(74) *Attorney, Agent, or Firm* — Armstrong Teasdale LLP

(57) ABSTRACT

A method for reducing phosphate absorption in a human or non-human animal subject at risk of developing or having developed hyperphosphatemia is disclosed. The method includes the step of administering orally to the subject an anti-intestinal sodium phosphate cotransporter type 2B (Npt2B) antibody in an amount effective to reduce or maintain the serum phosphate concentration in the subject.

33 Claims, 2 Drawing Sheets

(56) References Cited

OTHER PUBLICATIONS

Altschul, et al., (Nucleic Acids Res. 25, 3389-3402, 1997).
Polson, A., M.B. von Wechmar and M.H. van Regenmortel, "Isolation of Viral IgY Antibodies from Yolks of Immunized Hens," Immunological Communications 9:475-493 (1980).
Camenisch C et al., FASEB J. 1999, 13:81-88.
Akita E & Nakai S, J. Immunol. Methods 1993, 160:207-214.
Yokazawa, et al. Nephron 1986, 44:230-234.
Katsumata, et al. Kid Intl 2003, 64:441-450.
Levi R, et al. J Am Soc Nephrol 2006, 17:107-112.
Cozzolino M, et al., Kidney Int. 2003, 64:1653-61.
International Search Report and Written Opinion regarding PCT/US2007/082244, dated May 7, 2008.
Yudd, et al.: "Current medical management of secondary hyperparathyroidism" American Journal of Medical Sciences, vol. 320, No. 2, Aug. 2000, pp. 100-106.
Sogabe Natsuko, et al: "Enhancement by lactose if intestinal alkaline phosphatase expression in rats" Bone (New York), vol. 35, No. 1, Jul. 2004, pp. 249-255, XP002476363 ISSN: 8756-3282.
Roubaty, et al. "Relation between intestinal alkaline phosphatase activity and brush border membrane transport of inorganic phosphate, D-glucose, and D-glucose-6-phosphate" Pfluegers Archiv: European Journal of Physiology, vol. 412, No. 5, Oct. 1988, pp. 482-490.
Hirano, et al. "Role of Alkaline Phosphatase in Phosphate Uptake Into Brush Border Membrane Vesicles From Human Intestinal Mucosa" Journal of Biochemistry, vol. 97, No. 5, 1985, pp. 1461-1466.
Kovacs-Nolan, et al. "Microencapsulation for the gastric passage and controlled intestinal release of immunoglobulin Y" Journal of Immunological Methods, vol. 296, No. 1-2, Jan. 2005, pp. 199-209.
Schlemmer, et al. "Degradation of phytate in the gut of pigs—pathway of gastro-intestinal inositol phosphate hydrolysis and enzymes involved" Archiv Fuer Tierernaehrung—Archives of Animal Nutrition, vol. 55, No. 4, 2001, pp. 255-280.
Xu, et al., "Age-dependent regulation of rat intestinal type IIb sodium-phosphate cotransporter by 1,25-(OH)2 vitamin D3," American Journal of Physiology—Cell Physiology, 2005, vol. 282, No. 3, p. C487-C493.
Prie, et al., "Recent findings in phosphate homeostasis," Current Opinion in Nephrology and Hypertension, Jul. 2005, vol. 14, No. 4, p. 318-324.
Pileggi et al., Arch. Biochem. Biophys. 1995, 58:194-204.
Katai, et al., "Regulation of intestinal $Na^+$-dependent phosphate co-transporters by a low-phosphate diet and 1,25-dihydroxyvitamin D3," Biochemical Journal, Nov. 1, 1999, vol. 343, No. 3, p. 705-712.
International Search Report from PCT/US2007/082247, dated Apr. 23, 2008.
Fertel, et al., "Formation of Antibodies to Prostaglandins in the Yolk of Chicken Eggs," Biochemical and Biophysical Research Communications, vol. 102, No. 3, Oct. 15, 1981, p. 1028-1033.
Homann, et al., "Sodium-phosphate cotransporter in human salivary glands: Molecular evidence for the involvement of NPT2b in acinar phosphate secretion and ductal phosphate reabsorption," Archives of Oral Biology, Sep. 2005, vol. 50, No. 9, p. 759-768.
Karim-Jimenez, et al., "Molecular determinants for apical expression of teh renal type IIa Na<+>/Pi-cotransporter," Pflugers Archly European Journal of Physiology, 2001, vol. 442, No. 5, p. 782-790.
Stollar, et al., "Cross-reactions of nucleic acids with monoclonal antibodies to phosphatidylinositol phosphate and cholesterol," Molecular Immunology, Jan. 1, 1989, vol. 26, No. 1, p. 73-79.
Horie, et al., "Suppressive effect of functional drinking yogurt containing specific egg yolk immunoglobulin on Helicobacter pylori in humans," Journal of Dairy Science, Dec. 2004, vol. 87, No. 12, p. 4073-4079.
Schade, et al., "Chicken Egg Yolk Antibodies (IGY-Technology): A Review of Progress in Production and Use in Research and Human and Veterinary Medicine," Alternatives to Laboratory Animals, Apr. 1, 2005, vol. 33, No. 2, p. 129-154.
Levi, et al., "Renal phosphate-wasting disorders," Advances in Chronic Kidney Disease, Apr. 2006, vol. 13, No. 2, p. 155-165.
International Search Report from PCT/US2007/082236, dated Jun. 5, 2008.
Office Action received in JP Patent Application No. 2009-534819, mailed Feb. 26, 2013.
Miyamoto et al., "Inhibition of intestinal sodium-dependent inorganic phosphate transport by fibroblast growth factor 23," Therapeutic Apheresis and Dialysis, vol. 9(4), pp. 331-335 (2005).
Hattenhauer et al., "Regulation of small intestinal Na-P(i) type IIb cotransporter by dietary phosphate intake," American Journal of Physiology, vol. 277(4), pt. 1, pp. G756-G762 (1999).
Worledge et al., "Oral Administration of Avian Tumor Necrosis Factor Antibodies Effectively Treats Experimental Colitis in Rats," Digestive Diseases and Sciences, vol. 45(12), p. 22-98-2305 (2000).
Eto N., et al., "Nicotinamide prevents the development of hyperphosphataemia by suppressing intestinal sodium-dependent phosphate transporter in rats with adenine-induced renal failure," Nephrology Dialysis Transplantation (Jul. 2005), vol. 20, No. 7, p. 1378-1384.
Carlander, D., et al., "Peroral immunotheraphy with yolk antibodies for the prevention and treatment of enteric infections," Immunologic Research (2000), vol. 21, No. 1, p. 1-6.
Package insert for Rocaltrol (R) capsules, Chugai Pharmaceutical Co., Ltd. (Oct. 2005), 5th Edition, p. 1-3.
Office Action received in JP Patent Application No. 2009-534819, mailed Sep. 25, 2012.
Saito, H., et al., "Human Fibroblast Growth Factor-23 Mutants Suppress $Na^+$-dependent Phosphate Co-transport Activity and 1alpha,25-Dihydroxyvitamin D3 Production," J. Biol. Chem. 278(4):2206-2211 (Jan. 24, 2003).

* cited by examiner

SEQUENCE LISTING

<160> NUMBER OF SEQ ID NOS: 19

<210> SEQ ID NO 1
<211> LENGTH: 690
<212> TYPE: PRT
<213> ORGANISM: Homo sapiens

<400> SEQUENCE: 1

```
Met Ala Pro Trp Pro Glu Leu Gly Asp Ala Gln Pro Asn Pro Asp Lys
1               5                   10                  15

Tyr Leu Glu Gly Ala Ala Gly Gln Gln Pro Thr Ala Pro Asp Lys Ser
            20                  25                  30

Lys Glu Thr Asn Lys Thr Asp Asn Thr Glu Ala Pro Val Thr Lys Ile
        35                  40                  45

Glu Leu Leu Pro Ser Tyr Ser Thr Ala Thr Leu Ile Asp Glu Pro Thr
    50                  55                  60

Glu Val Asp Asp Pro Trp Asn Leu Pro Thr Leu Gln Asp Ser Gly Ile
65                  70                  75                  80

Lys Trp Ser Glu Arg Asp Thr Lys Gly Lys Ile Leu Cys Phe Phe Gln
                85                  90                  95

Gly Ile Gly Arg Leu Ile Leu Leu Gly Phe Leu Tyr Phe Phe Val
            100                 105                 110

Cys Ser Leu Asp Ile Leu Ser Ser Ala Phe Gln Leu Val Gly Gly Lys
        115                 120                 125

Met Ala Gly Gln Phe Phe Ser Asn Ser Ser Ile Met Ser Asn Pro Leu
    130                 135                 140

Leu Gly Leu Val Ile Gly Val Leu Val Thr Val Leu Val Gln Ser Ser
145                 150                 155                 160

Ser Thr Ser Thr Ser Ile Val Val Ser Met Val Ser Ser Ser Leu Leu
                165                 170                 175

Thr Val Arg Ala Ala Ile Pro Ile Ile Met Gly Ala Asn Ile Gly Thr
            180                 185                 190

Ser Ile Thr Asn Thr Ile Val Ala Leu Met Gln Val Gly Asp Arg Ser
        195                 200                 205

Glu Phe Arg Arg Ala Phe Ala Gly Ala Thr Val His Asp Phe Phe Asn
    210                 215                 220

Trp Leu Ser Val Leu Val Leu Pro Val Glu Val Ala Thr His Tyr
225                 230                 235                 240

Leu Glu Ile Ile Thr Gln Leu Ile Val Glu Ser Phe His Phe Lys Asn
                245                 250                 255

Gly Glu Asp Ala Pro Asp Leu Leu Lys Val Ile Thr Lys Pro Phe Thr
            260                 265                 270

Lys Leu Ile Val Gln Leu Asp Lys Lys Val Ile Ser Gln Ile Ala Met
        275                 280                 285

Asn Asp Glu Lys Ala Lys Asn Lys Ser Leu Val Lys Ile Trp Cys Lys
    290                 295                 300

Thr Phe Thr Asn Lys Thr Gln Ile Asn Val Thr Val Pro Ser Thr Ala
305                 310                 315                 320

Asn Cys Thr Ser Pro Ser Leu Cys Trp Thr Asp Gly Ile Gln Asn Trp
                325                 330                 335

Thr Met Lys Asn Val Thr Tyr Lys Glu Asn Ile Ala Lys Cys Gln His
            340                 345                 350

Ile Phe Val Asn Phe His Leu Pro Asp Leu Ala Val Gly Thr Ile Leu
        355                 360                 365
```

-continued

```
Leu Ile Leu Ser Leu Leu Val Leu Cys Gly Cys Leu Ile Met Ile Val
    370                 375                 380

Lys Ile Leu Gly Ser Val Leu Lys Gly Gln Val Ala Thr Val Ile Lys
385                 390                 395                 400

Lys Thr Ile Asn Thr Asp Phe Pro Phe Pro Phe Ala Trp Leu Thr Gly
                405                 410                 415

Tyr Leu Ala Ile Leu Val Gly Ala Gly Met Thr Phe Ile Val Gln Ser
            420                 425                 430

Ser Ser Val Phe Thr Ser Ala Leu Thr Pro Leu Ile Gly Ile Gly Val
        435                 440                 445

Ile Thr Ile Glu Arg Ala Tyr Pro Leu Thr Leu Gly Ser Asn Ile Gly
450                 455                 460

Thr Thr Thr Thr Ala Ile Leu Ala Ala Leu Ala Ser Pro Gly Asn Ala
465                 470                 475                 480

Leu Arg Ser Ser Leu Gln Ile Ala Leu Cys His Phe Phe Phe Asn Ile
                485                 490                 495

Ser Gly Ile Leu Leu Trp Tyr Pro Ile Pro Phe Thr Arg Leu Pro Ile
            500                 505                 510

Arg Met Ala Lys Gly Leu Gly Asn Ile Ser Ala Lys Tyr Arg Trp Phe
        515                 520                 525

Ala Val Phe Tyr Leu Ile Ile Phe Phe Leu Ile Pro Leu Thr Val
        530                 535                 540

Phe Gly Leu Ser Leu Ala Gly Trp Arg Val Leu Val Gly Val Gly Val
545                 550                 555                 560

Pro Val Val Phe Ile Ile Leu Val Leu Cys Leu Arg Leu Leu Gln
                565                 570                 575

Ser Arg Cys Pro Arg Val Leu Pro Lys Lys Leu Gln Asn Trp Asn Phe
        580                 585                 590

Leu Pro Leu Trp Met Arg Ser Leu Lys Pro Trp Asp Ala Val Val Ser
            595                 600                 605

Lys Phe Thr Gly Cys Phe Gln Met Arg Cys Cys Cys Cys Arg Val
610                 615                 620

Cys Cys Arg Ala Cys Cys Leu Leu Cys Gly Cys Pro Lys Cys Cys Arg
625                 630                 635                 640

Cys Ser Lys Cys Cys Glu Asp Leu Glu Glu Ala Gln Glu Gly Gln Asp
                645                 650                 655

Val Pro Val Lys Ala Pro Glu Thr Phe Asp Asn Ile Thr Ile Ser Arg
            660                 665                 670

Glu Ala Gln Gly Glu Val Pro Ala Ser Asp Ser Lys Thr Glu Cys Thr
        675                 680                 685

Ala Leu
    690

<210> SEQ ID NO 2
<211> LENGTH: 697
<212> TYPE: PRT
<213> ORGANISM: mouse

<400> SEQUENCE: 2

Met Ala Pro Trp Pro Glu Leu Glu Asn Ala Gln Pro Asn Pro Gly Lys
1               5                   10                  15

Phe Ile Glu Gly Ala Ser Gly Pro Gln Ser Ser Ile Pro Ala Lys Asp
            20                  25                  30

Lys Glu Ala Ser Lys Thr Asn Asp Asn Gly Thr Pro Val Ala Lys Thr
        35                  40                  45
```

```
Glu Leu Leu Pro Ser Tyr Ser Ala Leu Val Leu Ile Glu Glu His Pro
 50                  55                  60
Glu Gly Thr Asp Pro Trp Asp Leu Pro Glu Leu Gln Asp Thr Gly Ile
 65                  70                  75                  80
Lys Trp Ser Glu Arg Asp Thr Lys Gly Lys Thr Leu Cys Ile Phe Gln
                 85                  90                  95
Gly Val Gly Lys Phe Ile Leu Leu Gly Phe Leu Tyr Leu Phe Val
                100                 105                 110
Cys Ser Leu Asp Val Leu Ser Ser Ala Phe Gln Leu Val Gly Gly Lys
                115                 120                 125
Val Ala Gly Gln Phe Phe Ser Asn Asn Ser Ile Met Ser Asn Pro Val
130                 135                 140
Ala Gly Leu Val Ile Gly Val Leu Val Thr Val Met Val Gln Ser Ser
145                 150                 155                 160
Ser Thr Ser Ser Ser Ile Ile Val Ser Met Val Ala Ser Ser Leu Leu
                165                 170                 175
Thr Val Arg Ala Ala Ile Pro Ile Ile Met Gly Ala Asn Ile Gly Thr
                180                 185                 190
Ser Ile Thr Asn Thr Ile Val Ala Leu Met Gln Ala Gly Asp Arg Asn
                195                 200                 205
Glu Phe Arg Arg Ala Phe Ala Gly Ala Thr Val His Asp Phe Phe Asn
210                 215                 220
Trp Leu Ser Val Phe Val Leu Leu Pro Leu Glu Ala Ala Thr His Tyr
225                 230                 235                 240
Leu Glu Ile Leu Thr Asn Leu Val Leu Glu Thr Phe Lys Phe Gln Asn
                245                 250                 255
Gly Glu Asp Ala Pro Asp Ile Leu Lys Val Ile Thr Asp Pro Phe Thr
                260                 265                 270
Lys Leu Ile Ile Gln Leu Asp Lys Lys Val Ile Gln Gln Ile Ala Met
                275                 280                 285
Gly Asp Ser Ala Ala Gln Asn Lys Ser Leu Ile Lys Ile Trp Cys Lys
                290                 295                 300
Ser Ile Thr Asn Val Thr Glu Met Asn Val Thr Val Pro Ser Thr Asp
305                 310                 315                 320
Asn Cys Thr Ser Pro Ser Tyr Cys Trp Thr Asp Gly Ile Gln Thr Trp
                325                 330                 335
Thr Ile Gln Asn Val Thr Gln Lys Glu Asn Ile Ala Lys Cys Gln His
                340                 345                 350
Ile Phe Val Asn Phe Ser Leu Pro Asp Leu Ala Val Gly Ile Ile Leu
                355                 360                 365
Leu Thr Val Ser Leu Val Val Leu Cys Gly Cys Leu Ile Met Ile Val
                370                 375                 380
Lys Leu Leu Gly Ser Val Leu Arg Gly Gln Val Ala Thr Val Ile Lys
385                 390                 395                 400
Lys Thr Leu Asn Thr Asp Phe Pro Phe Pro Phe Ala Trp Leu Thr Gly
                405                 410                 415
Tyr Leu Ala Ile Leu Val Gly Ala Gly Met Thr Phe Ile Val Gln Ser
                420                 425                 430
Ser Ser Val Phe Thr Ser Ala Met Thr Pro Leu Ile Gly Ile Gly Val
                435                 440                 445
Ile Ser Ile Glu Arg Ala Tyr Pro Leu Thr Leu Gly Ser Asn Ile Gly
                450                 455                 460
```

```
Thr Thr Thr Thr Ala Ile Leu Ala Ala Leu Ala Ser Pro Gly Asn Thr
465                 470                 475                 480

Leu Arg Ser Ser Leu Gln Ile Ala Leu Cys His Phe Phe Asn Ile
            485                 490                 495

Ser Gly Ile Leu Leu Trp Tyr Pro Ile Pro Phe Thr Arg Leu Pro Ile
            500                 505                 510

Arg Leu Ala Lys Gly Leu Gly Asn Ile Ser Ala Lys Tyr Arg Trp Phe
            515                 520                 525

Ala Val Phe Tyr Leu Ile Phe Phe Phe Val Thr Pro Leu Thr Val
        530                 535                 540

Phe Gly Leu Ser Leu Ala Gly Trp Pro Val Leu Val Gly Val Gly Val
545                 550                 555                 560

Pro Ile Ile Leu Leu Leu Leu Val Leu Cys Leu Arg Met Leu Gln
            565                 570                 575

Phe Arg Cys Pro Arg Ile Leu Pro Leu Lys Leu Arg Asp Trp Asn Phe
            580                 585                 590

Leu Pro Leu Trp Met His Ser Leu Lys Pro Trp Asp Asn Val Ile Ser
        595                 600                 605

Leu Ala Thr Thr Cys Phe Gln Arg Arg Cys Cys Cys Cys Arg Val
610                 615                 620

Cys Cys Arg Val Cys Cys Met Val Cys Gly Cys Lys Cys Cys Arg Cys
625                 630                 635                 640

Ser Lys Cys Cys Arg Asp Gln Gly Glu Glu Glu Glu Lys Glu Gln
            645                 650                 655

Asp Ile Pro Val Lys Ala Ser Gly Ala Phe Asp Asn Ala Ala Met Ser
            660                 665                 670

Lys Glu Cys Gln Asp Glu Gly Lys Gly Gln Val Glu Val Leu Ser Met
            675                 680                 685

Lys Ala Leu Ser Asn Thr Thr Val Phe
            690                 695

<210> SEQ ID NO 3
<211> LENGTH: 695
<212> TYPE: PRT
<213> ORGANISM: rat

<400> SEQUENCE: 3

Met Ala Pro Trp Pro Glu Leu Glu Asn Ala His Pro Asn Pro Asn Lys
1               5                   10                  15

Phe Ile Glu Gly Ala Ser Gly Pro Gln Ser Ser Ile Pro Asp Lys Asp
            20                  25                  30

Lys Gly Thr Ser Lys Thr Asn Asp Ser Gly Thr Pro Val Ala Lys Ile
        35                  40                  45

Glu Leu Leu Pro Ser Tyr Ser Ala Leu Val Leu Ile Glu Glu Pro Pro
    50                  55                  60

Glu Gly Asn Asp Pro Trp Asp Leu Pro Glu Leu Gln Asp Asn Gly Ile
65                  70                  75                  80

Lys Trp Ser Glu Arg Asp Ser Lys Gly Lys Ile Leu Cys Ile Phe Gln
                85                  90                  95

Gly Ile Gly Lys Phe Ile Leu Leu Leu Gly Phe Leu Tyr Leu Phe Val
            100                 105                 110

Cys Ser Leu Asp Val Leu Ser Ser Ala Phe Gln Leu Val Gly Gly Lys
        115                 120                 125

Met Ala Gly Gln Phe Phe Ser Asn Asn Ser Ile Met Ser Asn Pro Val
130                 135                 140
```

-continued

```
Ala Gly Leu Val Ile Gly Val Leu Val Thr Val Met Val Gln Ser Ser
145                 150                 155                 160

Ser Thr Ser Ser Ser Ile Ile Val Ser Met Val Ala Ser Ser Leu Leu
            165                 170                 175

Ser Val Arg Ala Ala Ile Pro Ile Ile Met Gly Ala Asn Ile Gly Thr
        180                 185                 190

Ser Ile Thr Asn Thr Ile Val Ala Leu Met Gln Ala Gly Asp Arg Asn
            195                 200                 205

Glu Phe Arg Arg Ala Phe Ala Gly Ala Thr Val His Asp Phe Phe Asn
        210                 215                 220

Trp Leu Ser Val Leu Val Leu Pro Leu Glu Ala Ala Thr His Tyr
225                 230                 235                 240

Leu Glu Lys Leu Thr Asn Leu Val Leu Glu Thr Phe Ser Phe Gln Asn
                245                 250                 255

Gly Glu Asp Ala Pro Asp Ile Leu Lys Val Ile Thr Asp Pro Phe Thr
            260                 265                 270

Lys Leu Ile Ile Gln Leu Asp Lys Lys Val Ile Gln Gln Ile Ala Met
        275                 280                 285

Gly Asp Ser Glu Ala Gln Asn Lys Ser Leu Ile Lys Ile Trp Cys Lys
290                 295                 300

Thr Ile Ser Asn Val Ile Glu Glu Asn Val Thr Val Pro Ser Pro Asp
305                 310                 315                 320

Asn Cys Thr Ser Pro Ser Tyr Cys Trp Thr Asp Gly Ile Gln Thr Trp
                325                 330                 335

Thr Ile Gln Asn Val Thr Glu Lys Glu Asn Ile Ala Lys Cys Gln His
            340                 345                 350

Ile Phe Val Asn Phe Ser Leu Pro Asp Leu Ala Val Gly Ile Ile Leu
        355                 360                 365

Leu Thr Val Ser Leu Leu Ile Leu Cys Gly Cys Leu Ile Met Ile Val
    370                 375                 380

Lys Leu Leu Gly Ser Val Leu Arg Gly Gln Val Ala Thr Val Ile Lys
385                 390                 395                 400

Lys Thr Leu Asn Thr Asp Phe Pro Phe Pro Phe Ala Trp Leu Thr Gly
                405                 410                 415

Tyr Leu Ala Ile Leu Val Gly Ala Gly Met Thr Phe Ile Val Gln Ser
            420                 425                 430

Ser Ser Val Phe Thr Ser Ala Met Thr Pro Leu Ile Gly Ile Gly Val
        435                 440                 445

Ile Ser Ile Glu Arg Ala Tyr Pro Leu Thr Leu Gly Ser Asn Ile Gly
    450                 455                 460

Thr Thr Thr Thr Ala Ile Leu Ala Ala Leu Ala Ser Pro Gly Asn Thr
465                 470                 475                 480

Leu Arg Ser Ser Leu Gln Ile Ala Leu Cys His Phe Phe Asn Ile
                485                 490                 495

Ser Gly Ile Leu Leu Trp Tyr Pro Ile Pro Phe Thr Arg Leu Pro Ile
            500                 505                 510

Arg Leu Ala Lys Gly Leu Gly Asn Ile Ser Ala Lys Tyr Arg Trp Phe
        515                 520                 525

Ala Val Phe Tyr Leu Ile Phe Phe Leu Leu Thr Pro Leu Thr Val
    530                 535                 540

Phe Gly Leu Ser Leu Ala Gly Trp Pro Val Leu Val Gly Val Gly Val
545                 550                 555                 560
```

```
Pro Ile Ile Leu Leu Ile Leu Val Leu Cys Leu Arg Met Leu Gln
            565                 570                 575
Ala Arg Cys Pro Arg Ile Leu Pro Leu Lys Leu Arg Asp Trp Asn Phe
            580                 585                 590
Leu Pro Leu Trp Met His Ser Leu Lys Pro Trp Asp Asn Ile Ile Ser
            595                 600                 605
Leu Ala Thr Ser Cys Phe Gln Arg Arg Cys Cys Cys Cys Arg Val
            610                 615                 620
Cys Cys Arg Val Cys Cys Met Val Cys Gly Lys Cys Cys Arg Cys
625                 630                 635                 640
Ser Lys Cys Cys Lys Asn Leu Glu Glu Glu Glu Lys Glu Gln Asp Val
            645                 650                 655
Pro Val Lys Ala Ser Gly Gly Phe Asp Asn Thr Ala Met Ser Lys Glu
            660                 665                 670
Cys Gln Asp Glu Gly Lys Gly Gln Val Glu Val Leu Gly Met Lys Ala
            675                 680                 685
Leu Ser Asn Thr Thr Val Phe
            690                 695

<210> SEQ ID NO 4
<211> LENGTH: 674
<212> TYPE: PRT
<213> ORGANISM: chicken

<400> SEQUENCE: 4

Met Ala Pro Trp Pro Glu Val Asp Lys Pro Glu Thr Asn Asn Tyr Ile
1               5                   10                  15
Gly Asp Ser Ser Lys Gln Asn Gln Asn Met Ala Gly Lys Glu Gly Glu
                20                  25                  30
Asn His Lys Gly Asn Val Ala Ser Leu Gly Asn Lys Val Glu Ile Gln
            35                  40                  45
Pro Ala Phe Ser Thr Ile Ala Leu Ile Asp Glu Thr Arg Gln Glu Glu
        50                  55                  60
Asp Pro Trp Ala Leu Pro Glu Leu Gln Asp Thr Gly Val Lys Trp Ser
65                  70                  75                  80
Glu Leu Asp Arg Lys Gly Lys Ile Ile Arg Val Leu Tyr Gly Ile Gly
                85                  90                  95
Lys Phe Ile Met Leu Leu Gly Leu Leu Tyr Leu Phe Val Cys Ser Leu
                100                 105                 110
Asp Val Leu Ser Ser Ala Phe Gln Leu Val Gly Gly Lys Ala Ala Gly
            115                 120                 125
Asp Ile Phe Lys Asp Asp Ser Val Leu Ser Asn Pro Val Ala Gly Leu
        130                 135                 140
Val Ile Gly Val Leu Val Thr Val Met Val Gln Ser Ser Ser Thr Ser
145                 150                 155                 160
Ser Ser Ile Ile Val Ser Met Val Ser Ser Thr Leu Leu Thr Val Gln
                165                 170                 175
Ser Ala Ile Pro Ile Ile Met Gly Ala Asn Ile Gly Thr Ser Val Thr
            180                 185                 190
Asn Thr Ile Val Ala Leu Met Gln Ala Gly Asp Arg Asn Glu Phe Arg
        195                 200                 205
Arg Ala Phe Ala Gly Ala Thr Ile His Asp Phe Phe Asn Trp Leu Ala
    210                 215                 220
Val Phe Ala Leu Leu Pro Ile Glu Val Ile Ser Gly Tyr Leu Tyr His
225                 230                 235                 240
```

```
Leu Thr Asn Val Ile Val Glu Ser Phe His Leu Glu Ser Gly Glu Asp
                245                 250                 255

Ala Pro Glu Leu Leu Lys Val Ile Thr Asp Pro Phe Thr Lys Leu Ile
            260                 265                 270

Ile Glu Leu Asp Lys Ser Val Ile Asn Ala Ile Ala Thr Asn Asp Glu
        275                 280                 285

Ser Ala Lys Asn Lys Ser Leu Val Lys Val Trp Cys Ile Thr Glu Thr
    290                 295                 300

Asn Val Thr Leu Gln Asn Val Thr Ile Pro Pro Ser Glu Asn Cys Thr
305                 310                 315                 320

Ser Ser Glu Leu Cys Trp Ser Glu Gly Asn Val Thr Trp Thr Met Lys
                325                 330                 335

Asn Ile Ser Glu Thr Glu Tyr Ile Thr Lys Cys Arg His Leu Phe Ala
            340                 345                 350

Glu Thr Asp Leu Pro Asp Leu Ala Ile Gly Leu Ile Leu Leu Ala Leu
        355                 360                 365

Ser Leu Leu Val Leu Cys Ser Cys Leu Val Met Ile Val Lys Leu Leu
    370                 375                 380

Asn Ser Val Leu Lys Gly Gln Val Ala Ser Val Ile Lys Lys Thr Ile
385                 390                 395                 400

Asn Thr Asp Phe Pro Phe Pro Phe Thr Trp Leu Ala Gly Tyr Leu Ala
                405                 410                 415

Met Leu Ala Gly Ala Gly Met Thr Phe Val Val Gln Ser Ser Ser Val
            420                 425                 430

Phe Thr Ser Ala Ile Thr Pro Leu Val Gly Ile Gly Val Ile Ser Ile
        435                 440                 445

Glu Arg Ser Tyr Pro Leu Thr Leu Gly Ala Asn Ile Gly Thr Thr Thr
    450                 455                 460

Thr Ala Ile Leu Ala Ala Leu Ala Ser Pro Gly Ser Thr Leu Lys Tyr
465                 470                 475                 480

Ser Leu Gln Ile Ala Leu Cys His Phe Phe Phe Asn Val Ser Gly Ile
                485                 490                 495

Ile Leu Phe Tyr Pro Leu Pro Phe Thr Arg Leu Pro Ile Arg Met Ser
            500                 505                 510

Lys Ser Leu Gly Asn Ile Thr Ala Lys Tyr Arg Trp Phe Ala Ile Phe
        515                 520                 525

Tyr Leu Leu Ile Cys Phe Phe Leu Pro Leu Phe Val Phe Gly Leu
    530                 535                 540

Ser Leu Ala Gly Trp Pro Val Leu Leu Gly Val Cys Leu Pro Leu Leu
545                 550                 555                 560

Ala Leu Phe Ile Ala Val Ile Val Ile Asn Ile Met Gln Thr Arg Arg
                565                 570                 575

Pro His Ser Leu Pro Glu Lys Leu Gln Asn Trp Asp Phe Leu Pro Ile
            580                 585                 590

Trp Met His Ser Leu Glu Pro Trp Asp Asn Met Ile Met Ser Ser Leu
        595                 600                 605

Ala Phe Cys Gly Lys His Cys Cys Gly Phe Cys Lys Cys Cys Lys Val
    610                 615                 620

Asn Ala Glu Gln Glu Gly Ala Lys Asp Asn Gln Leu Lys Thr Met Glu
625                 630                 635                 640

Val Tyr Glu Asn Thr Ile Ala Met Ala Asp Glu Glu Arg Gly Val Arg
                645                 650                 655
```

-continued

```
Arg Ala Pro Ala Ala Cys Val Glu Lys Thr Gly Thr Asn Asn Thr
            660                 665                 670

Ala Leu

<210> SEQ ID NO 5
<211> LENGTH: 8
<212> TYPE: PRT
<213> ORGANISM: Artificial
<220> FEATURE:
<223> OTHER INFORMATION: synthetic peptide

<400> SEQUENCE: 5

Leu Val Gly Gly Lys Met Ala Gly
1               5

<210> SEQ ID NO 6
<211> LENGTH: 8
<212> TYPE: PRT
<213> ORGANISM: Artificial
<220> FEATURE:
<223> OTHER INFORMATION: synthetic peptide

<400> SEQUENCE: 6

Phe His Phe Lys Asn Gly Glu Asp
1               5

<210> SEQ ID NO 7
<211> LENGTH: 8
<212> TYPE: PRT
<213> ORGANISM: Artificial
<220> FEATURE:
<223> OTHER INFORMATION: synthetic peptide

<400> SEQUENCE: 7

Leu Lys Val Ile Thr Lys Pro Phe
1               5

<210> SEQ ID NO 8
<211> LENGTH: 8
<212> TYPE: PRT
<213> ORGANISM: Artificial
<220> FEATURE:
<223> OTHER INFORMATION: synthetic peptide

<400> SEQUENCE: 8

Leu Asp Lys Lys Val Ile Ser Gln
1               5

<210> SEQ ID NO 9
<211> LENGTH: 8
<212> TYPE: PRT
<213> ORGANISM: Artificial
<220> FEATURE:
<223> OTHER INFORMATION: synthetic peptide

<400> SEQUENCE: 9

Ser Leu Val Lys Ile Trp Cys Lys
1               5

<210> SEQ ID NO 10
<211> LENGTH: 8
<212> TYPE: PRT
<213> ORGANISM: Artificial
<220> FEATURE:
<223> OTHER INFORMATION: synthetic peptide

<400> SEQUENCE: 10
```

```
Thr Ser Pro Ser Leu Cys Trp Thr
1               5

<210> SEQ ID NO 11
<211> LENGTH: 8
<212> TYPE: PRT
<213> ORGANISM: Artificial
<220> FEATURE:
<223> OTHER INFORMATION: synthetic peptide

<400> SEQUENCE: 11

Tyr Pro Leu Thr Leu Gly Ser Asn
1               5

<210> SEQ ID NO 12
<211> LENGTH: 8
<212> TYPE: PRT
<213> ORGANISM: Artificial
<220> FEATURE:
<223> OTHER INFORMATION: synthetic peptide

<400> SEQUENCE: 12

Thr Thr Ala Ile Leu Ala Ala Leu
1               5

<210> SEQ ID NO 13
<211> LENGTH: 8
<212> TYPE: PRT
<213> ORGANISM: Artificial
<220> FEATURE:
<223> OTHER INFORMATION: synthetic peptide

<400> SEQUENCE: 13

Val Gln Ser Ser Ser Val Phe Thr
1               5

<210> SEQ ID NO 14
<211> LENGTH: 8
<212> TYPE: PRT
<213> ORGANISM: Artificial
<220> FEATURE:
<223> OTHER INFORMATION: synthetic peptide

<400> SEQUENCE: 14

Leu Ile Gly Ile Gly Val Ile Thr
1               5

<210> SEQ ID NO 15
<211> LENGTH: 8
<212> TYPE: PRT
<213> ORGANISM: Artificial
<220> FEATURE:
<223> OTHER INFORMATION: synthetic peptide

<400> SEQUENCE: 15

Glu Val Ala Thr His Tyr Leu Glu
1               5

<210> SEQ ID NO 16
<211> LENGTH: 8
<212> TYPE: PRT
<213> ORGANISM: Artificial
<220> FEATURE:
<223> OTHER INFORMATION: synthetic peptide

<400> SEQUENCE: 16
```

```
Gly Ile Gln Asn Trp Thr Met Lys
1               5

<210> SEQ ID NO 17
<211> LENGTH: 8
<212> TYPE: PRT
<213> ORGANISM: Artificial
<220> FEATURE:
<223> OTHER INFORMATION: synthetic peptide

<400> SEQUENCE: 17

Phe Val Asn Phe His Leu Pro Asp
1               5

<210> SEQ ID NO 18
<211> LENGTH: 8
<212> TYPE: PRT
<213> ORGANISM: Artificial
<220> FEATURE:
<223> OTHER INFORMATION: synthetic peptide

<400> SEQUENCE: 18

Ser Pro Gly Asn Ala Leu Arg Ser
1               5

<210> SEQ ID NO 19
<211> LENGTH: 8
<212> TYPE: PRT
<213> ORGANISM: Artificial
<220> FEATURE:
<223> OTHER INFORMATION: synthetic peptide

<400> SEQUENCE: 19

Glu Asn Ile Ala Lys Cys Gln His
1               5
```

US 8,802,094 B2

METHOD OF REDUCING PHOSPHATE ABSORPTION BY ADMINISTERING ORALLY AN IGY ANTI-INTESTINAL SODIUM PHOSPHATE COTRANSPORTER TYPE 2B ANTIBODY

CROSS-REFERENCE TO RELATED APPLICATIONS

This application is a U.S. National Phase patent application of International Application Serial Number PCT/US2007/082247, filed on Oct. 23, 2007, which is herein incorporated by reference in its entirety, and which claims the benefit of U.S. provisional application Ser. No. 60/862,876, filed on Oct. 25, 2006, which is herein incorporated by reference in its entirety.

STATEMENT REGARDING FEDERALLY SPONSORED RESEARCH OR DEVELOPMENT

Not applicable.

REFERENCE TO A SEQUENCE LISTING

This application includes a Sequence Listing. A paper copy and a computer readable copy of the Sequence Listing in a .txt file are being submitted concurrently herewith. The information contained in the Sequence Listing is herein incorporated by reference in its entirety.

BACKGROUND OF THE INVENTION

Phosphorus is an essential element in human nutrition and plays essential structural and functional roles in the biochemistry, cellular integrity, and physiological processes of the body. In foods comprising animal or vegetable matter, phosphorus can be found as inorganic phosphate (Pi) (e.g., in its pentavalent form in combination with oxygen as phosphate ($PO_4^{3-}$)), which can be readily absorbed from the gastrointestinal tract. Also, phosphate can be found as a constituent of bio-macromolecules such as proteins, nucleic acids, lipids and sugars. Plant material can also be enriched in phytic acid ($C_6H_6[OPO(OH)_2]_6$), which is the principal storage form of phosphate (phytic phosphate) in many plant tissues (e.g., bran and seeds), accounting for 70% to 80% of phosphate in plants. Phytic acid or salts thereof (phytate) typically cannot be absorbed by monogastric animals and will pass out with the feces. Phytic acid/phytate can account for approximately 25% of an adult's daily dietary phosphate intake.

Phosphate is an essential component of bone mineral, as approximately 85% of phosphate in the adult body is in mineralized extracellular matrix, such as bone and teeth. Approximately 15% of phosphate is intracellular (e.g., in soft tissues) and about 0.1% is found in extracellular fluids (Tenenhouse et al., Vitamin D, 2nd edition, Elsevier, 2005). Cellular phosphate can also be found in the form of phospholipids which make up the structure of cellular membranes. Phosphate is also an essential structural component of nucleic acids such as DNA and RNA as well as nucleotides such as adenosine triphosphate (ATP) which is an important energy storage and transfer molecule and cyclic adenosine monophosphate which is an important cellular signaling molecule. Other physiological functions of intracellular phosphate include the following: (1) phosphorylation of a number of protein enzymes, hormones and cell signaling molecules for their activation; (2) maintaining normal acid-base balance as a physiological buffer; and (3) comprising the phosphate-containing molecule 2,3-diphosphoglycerate (2,3-DPG) in red blood cells. An average human contains about 700 to 1,000 grams of phosphorus (Lau K., Phosphate Disorders. Saunders; 1986:398-470), and consumes and excretes about one gram to about three grams of phosphorus per day in the form of $PO_4^{3-}$.

Humans maintain phosphate homeostasis by at least three routes—the gastrointestinal tract, kidneys, and bone. The gastrointestinal tract participates in phosphate homeostasis as an organ of phosphate absorption and excretion/resorption. Bone serves as a reservoir of phosphate which can be mobilized in response to various physiological signals. Gastrointestinal absorption of dietary phosphate is very efficient, with the principal sites of absorption being the duodenum and the jejunum (Delmez J A et al., Am J Kidney Dis, 1992, 19:303-317). A variable amount of dietary phosphate (10% to 80% of the ingested amount) is excreted in feces, depending on whether the diet is of plant origin (largely inaccessible phosphate) or animal tissue origin (largely digestible). Inorganic phosphate in food is absorbed in two ways, an active transcellular route via the brush border membrane and a passive paracellular route via tight junctions between cells (Cross et al., Miner Electrolyte Metab 1990, 16:115-124, and Walton J et al., Clin Sci 1979, 56:407-412). Some reports based on rat studies indicate that colonic phosphate transport is mediated mainly through the paracellular diffusive pathway (Hu et al., Miner Electrolyte Metab, 1997, 23:7-12; and Peters et al., Res Exp Med (Berl), 1988, 188:139-149). Other reports based on rat studies suggest that transcellular active transport is the dominant route in phosphate absorption across small intestine (Eto et al., Drug Metab Pharmacokinet, 2006, 21:217-221).

The kidney participates in phosphate homeostasis as an organ of phosphate filtration, reabsorption and excretion. The kidney is the main regulatory organ that maintains phosphate homeostasis. In healthy adult individuals, daily renal phosphate excretion equals the amount of daily gastrointestinal phosphate absorption. However, in states of phosphate depletion, the kidneys reduce urinary phosphate excretion to virtually zero (Knox F et al., Am. J. Physiol. 1977, 233:F261-F268). Renal phosphate reabsorption occurs mainly in the proximal tubule. The fractional urinary excretion of phosphate can vary between 0.1% to 20%, thus representing a powerful homeostatic mechanism. In severe renal failure, such as that resulting from chronic kidney disease, hyperphosphatemia occurs from inadequate renal phosphate clearance.

Primary regulatory factors of phosphate homeostasis are serum phosphate and parathyroid hormone (PTH). Increased serum phosphate levels enhance urinary excretion of phosphate. PTH decreases tubular phosphate reabsorption and increasing excretion of soluble phosphate into the urine. Other factors that affect phosphate homeostasis include, but are not limited to, age, diet (i.e. amount of phosphate ingested and/or chemical form of phosphate ingested), disease, pharmaceutical agents and diurnal variation.

Vitamin D, especially its active form 1,25-dihydroxyvitamin D (also called calcitriol), can also affect phosphate homeostasis by directly stimulating intestinal absorption of phosphate. In addition, vitamin D enhances bone resorption through mobilization of calcium and phosphate into the plasma (Albaaj F & Hutchison A, Drugs 2003, 63:577-596).

An example of abnormal phosphate homeostasis is hyperphosphatemia, which can occur by one or more of the following three mechanisms. The first mechanism is excessive phosphate absorption. The second mechanism is decreased phosphate excretion. The third mechanism is shifting phosphate from intracellular spaces to extracellular spaces. Severe hyperphosphatemia can cause paralysis, convulsions and cardiac arrest. Hyperphosphatemia occurs at serum phosphate concentrations above 5 mg/dl, which is associated with an increased risk of death (Block G et al., J. Am. Soc. Nephrol. 2004, 15:2208-2218). A normal physiological serum phosphate concentration is generally considered to be a serum phosphate concentration between about 2.4 mg/dl to about 4.5 mg/dl (Block G & Port F, Am. J. Kidney Dis. 2000, 35:1226-1237).

Patients with impaired kidney function can develop hyperphosphatemia as a result of decreased phosphate excretion by the kidney. Hyperphosphatemia ensues either when the vascular supply to the kidneys becomes reduced or when the glomeruli become damaged and cease filtering phosphate from the blood. As such, hyperphosphatemia is a predictable consequence of kidney disease and most kidney disease patients either have or will develop hyperphosphatemia. Examples of such kidney diseases include, but are not limited to, end stage renal disease, acute renal failure, chronic renal failure, polycystic kidney disease, chronic kidney disease, acute tubular necrosis (e.g., renal artery stenosis), infections that reduce kidney function (e.g., septicemia or kidney infection such as acute pyelonephritis), kidney transplantation rejection, and urinary tract obstruction.

Hyperphosphatemia associated with chronic kidney disease leads to severe pathophysiologies in calcium and phosphate homeostasis, especially if present over extended periods of time. Such pathophysiologies include, but are not limited to, hyperparathyroidism, bone disease (e.g., renal osteodystrophy) and calcification in joints, lungs, eyes and vasculature. Hyperphosphatemia in patients with chronic kidney disease is independently associated with mortality risk and the exact mechanism by which hyperphosphatemia increases mortality risk is unknown. For individuals who exhibit renal insufficiency, an elevation of serum phosphate within the normal range has been associated with progression of renal failure and increased risk of cardiovascular events. The National Kidney Foundation Kidney Disease Outcomes Quality Initiative Clinical Practice Guidelines for Bone Metabolism and Disease in Chronic Kidney Disease recommends maintenance of serum phosphate below 5.5 mg/dl, calcium-phosphate (Ca X P) product less than 55 mg$^2$/dl$^2$, and intact parathyroid hormone (iPTH) between 150 pg/ml and 300 pg/ml. Although the etiology is not fully demonstrated, high calcium-phosphate product has been held responsible for soft tissue calcification and cardiovascular disease. Cardiovascular disease is the cause of death in almost half of all dialysis patients.

Many kidney disease patients need to take an active form of vitamin D such as 1α,25-dihydroxyvitamin D$_3$ for maintaining calcium homeostasis and/or for treating or preventing hypocalcemia and/or secondary hyperparathyroidism because these patients are deficient in active vitamin D. Vitamin D$_3$ is first metabolized to 25-hydroxyvitamin D$_3$ (also called calcidiol) in the liver and subsequently to 1α,25-dihydroxyvitamin D$_3$ in the kidney. 1α,25-dihydroxyvitamin D$_3$ is much more active than 25-hydroxyvitamin D$_3$. Kidneys with impaired function cannot convert 25-hydroxyvitamin D$_3$ to 1α,25-dihydroxyvitamin D$_3$. The low 1α,25-dihydroxyvitamin D$_3$ level stimulates the parathyroid gland to secret more PTH and parathyroid hyperplasia and secondary hyperparathyroidism ensue. Standard treatment of secondary hyperparathyroidism in individuals with chronic kidney disease includes active vitamin D or its analogs. Likewise, approximately 70% of individuals with end stage renal disease or failure receive some form of vitamin D. As discussed above, vitamin D stimulates intestinal absorption of phosphate. Therefore, kidney disease patients who take vitamin D such as 1α,25-dihydroxyvitamin D$_3$ are more susceptible to hyperphosphatemia and can also have their existing hyperphosphatemia exacerbated due to a combination of increased phosphate absorption with concomitant decreased phosphate excretion.

Therapeutic efforts to reduce serum phosphate levels include, but are not limited to, dialysis, reduction in dietary phosphate intake, administration of nicotinamide, and oral administration of insoluble phosphate binders. Examples of insoluble phosphate binders include, but are not limited to, aluminum compounds (e.g., Amphojel® aluminum hydroxide gel), calcium compounds (e.g., calcium carbonate, acetate such as PhosLo® calcium acetate tablets, citrate, alginate, and ketoacid salts), anion exchange polymers (e.g., amine functional polymers described in U.S. Pat. Nos. 5,985,938, 5,980,881, 6,180,094, 6,423,754, and PCT publication WO 95/05184, Dowex® anion-exchange resins in the chloride form, RenaGel®, and polymer bound guanidinium hydrochloride), inorganic compounds such as lanthanum carbonate tetrahydrate (Fosrenal™), ferric salts of citrate and acetate, and a lanthanum based porous ceramic material (RenaZorb™).

BRIEF SUMMARY OF THE INVENTION

In one aspect, the present invention relates to a method for reducing phosphate absorption in a human or non-human animal subject at risk of developing or having developed hyperphosphatemia. The method includes the step of administering orally to the subject an anti-intestinal sodium phosphate cotransporter type 2B (Npt2B) antibody (e.g., an antibody that binds to an extracellular loop of intestinal Npt2B) in an amount effective to reduce or maintain the serum phosphate concentration in the subject. The antibody can be an IgY antibody or an antibody that binds to an epitope within amino acids 234-362 or amino acids 429-485 of the human intestinal Npt2B protein defined by SEQ ID NO:1. The method may further include the step of observing a decrease or stabilization of the serum phosphate concentration. For example, the serum phosphate concentrations before and after the antibody treatment can be measured and compared.

In another aspect, the present invention relates to a method for reducing side effects of vitamin D therapy in a human subject (e.g., a human subject who has a kidney disease, a vitamin D deficiency, or both). The method includes the step of administering orally to the subject (a) a vitamin D compound and (b) an anti-intestinal Npt2B antibody such as an anti-human intestinal Npt2B (SEQ ID NO:1) antibody wherein the antibody is administered in an amount effective to reduce hyperphosphatemia induced by vitamin D therapy. For example, the serum phosphate level of the subject can be reduced or maintained. In one embodiment, the antibody is an IgY antibody. In another embodiment, the antibody binds to an epitope within amino acids 234-362 or amino acids 429-485 of the human intestinal Npt2B protein defined by SEQ ID NO:1. The method may further include the step of observing a decrease or stabilization of the serum phosphate concentration. For example, the serum phosphate concentrations before and after the antibody treatment can be measured and compared.

The methods disclosed here can be used to attenuate or prevent hyperphosphatemia. In some embodiments, the serum phosphate concentration is reduced to or maintained at a level of or lower than about 150%, 125%, 120%, 115%, 110%, or 105% of a maximum physiological serum phosphate concentration in the accepted normal range. In some embodiments, the serum phosphate concentration is reduced to or maintained at a level within the normal range. For a human subject, the maximum high-normal serum phosphate concentration is 5.0 mg/dl. In a preferred embodiment, the serum phosphate concentration is reduced to or maintained at 5.5 mg/dl or lower or 5.0 mg/dl or lower in a human subject.

In some embodiments of the methods disclosed here, the subject has a kidney disease, receives a vitamin D compound (e.g., 1α,25-dihydroxyvitamin $D_3$), or both. In some embodiments, the subject is a human kidney disease patient who takes a vitamin D compound (e.g., 1α,25-dihydroxyvitamin $D_3$) and has a serum phosphate level above 5.0 mg/dl or 5.5 mg/dl. Examples of kidney diseases include end stage renal disease, acute renal failure, polycystic kidney disease, chronic kidney disease, acute tubular necrosis, infections that reduce kidney function (e.g., septicemia or kidney infection such as acute pyelonephritis), kidney transplantation rejection, or urinary tract obstruction.

In some embodiments of the methods disclosed here, the anti-intestinal Npt2B antibody is administered concomitantly with a phosphate binder. In some embodiments, the anti-intestinal Npt2B antibody is administered with food or close in time (i.e. within about one hour before or after) to the consumption of a food.

DETAILED DESCRIPTION OF THE INVENTION

Figure 1:
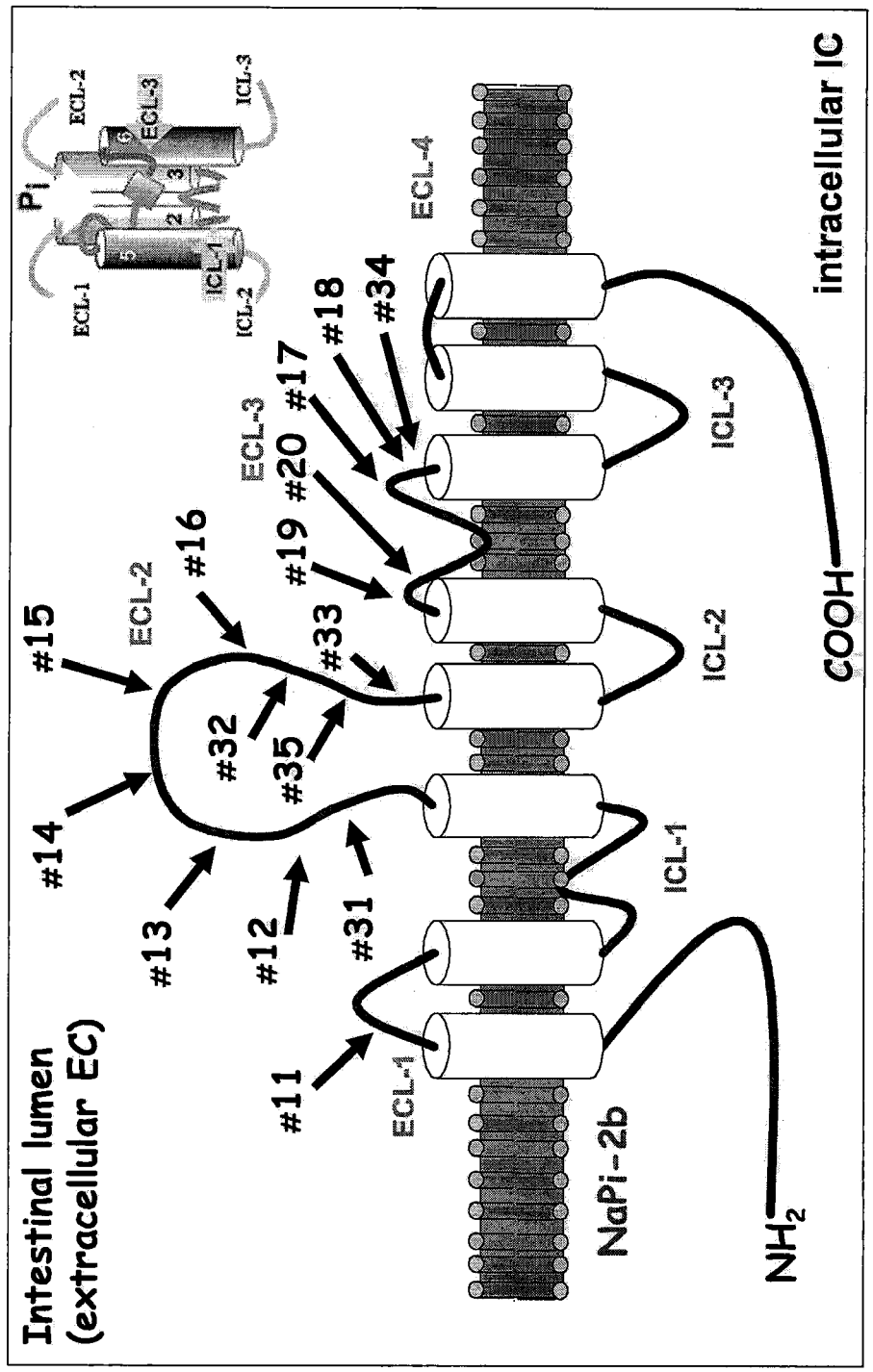
FIG. 1 is a peptide antigen map of human intestinal Npt2B. Extracellular (ECL1-ECL4) and intracellular (ICL1-ICL3) loops as well as transmembrane domains (1-8) of human intestinal Npt2B are shown. Numbers 11-20 and 31-35 show where the antigen peptides used to generate antibodies are located on the extracellular loops.

It is disclosed here that certain anti-intestinal Npt2B antibodies can be administered orally to a human or non-human animal subject to reduce phosphate absorption in the subject. Npt2B is associated with the intestinal brush border membrane (Hilfiker H et al., Proc Natl Acad Sci USA. 1998, 95:14564-14569). The prior art suggests that an anti-intestinal Npt2B antibody would not be effective for blocking Npt2B activity in vivo because the intestinal brush border membrane is coated with a mucus layer permeable only to low molecular weight solutes but not large macromolecules (e.g., antibodies/proteins) in order to protect the mucosal surface from degradation by proteolytic enzymes in the intestinal lumen (Atuma et al, Am J Physiol Gastrointest Liver Physiol 2001, 280:922; and M. Mantle and A. Allen, 1989, Gastrointestinal mucus, pp 202-229 in Gastrointestinal Secretions, J. S. Davison, ed., Butterworth and Co., Great Britain). In addition, it is uncertain whether a particular antibody administered orally can survive the acidic environment of the stomach and remain active. Despite the prior art evidence to the contrary, the inventors have shown, using antibodies to intestinal Npt2B as well as another intestinal brush border membrane-associated protein intestinal alkaline phosphatase (Nakano et al., Arch Histol Cytol 2001, 64:483-491), that orally administered antibodies can reach and block the activity of an intestinal brush border membrane-associated protein (examples below). In the examples below, the inventors have shown that orally administered anti-intestinal Npt2B antibodies can lower plasma phosphate levels, reduce body weight gain, reduce bone ash, and increase excreta phosphate.

Unless defined otherwise, all technical and scientific terms used herein have the same meaning as commonly understood by one of ordinary skill in the art to which the invention belongs. Although any methods and materials similar to or equivalent to those described herein can be used in the practice or testing of the present invention, the preferred methods and materials are now described.

In describing the embodiments and claiming the invention, the following terminology are used in accordance with the definitions set forth below.

As used herein, "antibody" includes an immunoglobulin molecule immunologically reactive with a particular antigen, and includes both polyclonal and monoclonal antibodies. The term also includes genetically engineered forms such as chimeric antibodies (e.g., humanized murine antibodies) and heteroconjugate antibodies (e.g., bispecific antibodies). The term also includes bivalent or bispecific molecules, diabodies, triabodies, and tetrabodies. Bivalent and bispecific molecules are described in, e.g., Kostelny et al., J Immunol 1992, 148:1547; Pack and Pluckthun, Biochemistry 1992, 31:1579; Zhu et al., Protein Sci 1997, 6:781; Hu et al., Cancer Res. 1996, 56:3055; Adams et al., Cancer Res. 1993, 53:4026; and McCartney et al., Protein Eng. 1995, 8:301. The term "antibody" also includes antigen binding forms of antibodies such as fragments with antigen-binding capability (e.g., Fab', F(ab')$_2$, Fab, Fv and rIgG). The term also refers to recombinant single chain Fv fragments (scFv). In addition, the term "antibody" encompasses an antibody having a stabilizing group covalently linked thereto to make the antibody more stable. Antibodies with an affinity Kd of $10^{-4}$ M or less can be employed in the present invention. Preferably, antibodies with an affinity Kd of $\leq 10^{-5}$ M or $\leq 10^{-6}$ M are employed. More preferably, antibodies with an affinity Kd of $\leq 10^{-7}$ M, $\leq 10^{-8}$ M, or $\leq 10^{-9}$ M are employed.

As used herein, the term "hyperphosphatemia" is used broadly to describe a condition in a subject wherein serum phosphate is present at a concentration above the medically accepted normal range.

As used herein, the term "attenuate" or "prevent" means achieving a therapeutic benefit or a prophylactic benefit. By therapeutic benefit, we mean amelioration or eradication of the underlying disorder being treated. For example, in a subject having hyperphosphatemia, therapeutic benefit includes amelioration or eradication of the underlying hyperphosphatemia. Also, a therapeutic benefit includes amelioration or eradication of one or more of the pathophysiological symptoms associated with the underlying disorder, such that an improvement is observed in the subject, notwithstanding that the subject may still be afflicted with the underlying disorder. For example, in a patient suffering from renal insufficiency and/or hyperphosphatemia, a therapeutic benefit refers to not only a decrease in the patient's serum phosphate level but also an improvement in the patient with respect to other disorders that accompany renal failure and/or hyperphosphatemia such as ectopic calcification and renal osteodystrophy. For prophylactic benefit, an antibody according to the present invention is administered to a patient at risk of developing hyperphosphatemia or to a patient reporting one or more of the pathophysiological symptoms of hyperphosphatemia even though a diagnosis of hyperphosphatemia may not have been made. For example, an antibody according to the present invention can be administered to a patient with chronic kidney disease where hyperphosphatemia has not been diagnosed. Prophylactic benefit includes prevention or delay of hyperphosphatemia.

As used herein, an effective amount of an antibody is an amount that lowers serum phosphate in a subject having hyperphosphatemia, prevents serum phosphate from rising in a subject having or at risk of having hyperphosphatemia, or reduces the absorption of phosphate from food which can be measured, for example, by increased fecal phosphate or by lowered or stabilized serum phosphate level.

As used herein, "kidney disease" refers to any disease or disorder that affects the function of the kidneys including those diseases of the kidney that result in poor phosphate filtration and includes diseases that affect blood supply to the kidney, as well as functional and structural defects in the kidneys. Examples of kidney disease include, but are not limited to, end stage renal disease, acute renal failure, chronic renal failure, polycystic kidney disease, chronic kidney disease (e.g., stage I, II, III, IV, or V chronic kidney disease as classified under the National Kidney Foundation Kidney Disease Outcomes Quality Initiative Clinical Practice Guidelines, which manifests as renal insufficiency and in later stages renal failure), acute tubular necrosis (e.g., renal artery stenosis), infections that reduce kidney function (e.g., septicemia or kidney infection such as acute pyelonephritis), kidney transplantation rejection, and urinary tract obstruction.

As used herein, the term "Vitamin D" refers broadly to the organic compounds named Vitamin $D_2$, Vitamin $D_3$, Vitamin $D_4$, etc., and to their metabolites and hormonal forms that influence calcium and phosphate homeostasis. Examples of vitamin D compounds include, but are not limited to, vitamin $D_2$ (ergocalciferol), 25-hydroxyvitamin $D_2$, 1α,25-dihydroxyvitamin $D_2$, vitamin $D_3$ (cholecalciferol), 25-hydroxyvitamin $D_3$, 1α,25-dihydroxyvitamin $D_3$, an analog of any of the forgoing or which can substantially occupy the intracellular vitamin D receptor, and those described in Bouillon et al., Endocrine Reviews 1995, 16: 200-257, which is herein incorporated by reference in its entirety. Vitamin D compounds also include those that are currently commercially available or in clinical trials including, but not limited to, 19-nor-1α,25 dihydroxyvitamin $D_2$ (Paricalcitol), 1α-hydroxyvitamin $D_2$ (Doxercalciferol), 1α-hydroxyvitamin $D_3$ (Alfacalcidol), investigational drugs from Leo Pharmaceutical including EB 1089 (Seocalcitol), KH 1060 (20-epi-22-oxa-24a,26a,27a-trihomo-1α,25-dihydroxy-$D_3$), MC 1288 and MC 903 (Calcipotriol), Roche Pharmaceutical drugs that include 1,25-dihydroxy-16-ene-$D_3$, 1,25-dihydroxy-16-ene-23-yne-$D_3$, and 25-dihydroxy-16-ene-23-yne-$D_3$, Chugai Pharmaceuticals 22-oxacalcitriol (22-oxa-1α,25-dihydroxy-$D_3$), 1αhydroxy $D_5$ from the University of Illinois, drugs from the Institute of Medical Chemistry—Schering AG that include ZK 161422 and ZK 157202.

In one aspect, the present invention relates to a method for reducing phosphate absorption in a human or non-human animal subject at risk of developing or having developed hyperphosphatemia. The method includes the step of administering orally to the subject an anti-intestinal sodium phosphate cotransporter type 2B (Npt2B) antibody (e.g., an antibody that binds to an extracellular loop of intestinal Npt2B) in an amount effective to reduce or maintain the serum phosphate concentration in the subject. The antibody can be an IgY antibody or an antibody that binds to an epitope within amino acids 234-362 or amino acids 429-485 of the human intestinal Npt2B protein defined by SEQ ID NO:1. The method may further include the step of observing a decrease or stabilization of the serum phosphate concentration. For example, the serum phosphate concentrations before and after the antibody treatment can be measured and compared.

In another aspect, the present invention relates to a method for reducing side effects of vitamin D therapy in a human subject (e.g., a human subject who has a kidney disease, a vitamin D deficiency, or both). The method includes the step of administering orally to the subject (a) a vitamin D compound and (b) an anti-intestinal Npt2B antibody such as an anti-human intestinal Npt2B (SEQ ID NO:1) antibody wherein the antibody is administered in an amount effective to reduce hyperphosphatemia induced by vitamin D therapy. For example, the serum phosphate level of the subject can be reduced or maintained. In one embodiment, the antibody is an IgY antibody. In another embodiment, the antibody binds to an epitope within amino acids 234-362 or amino acids 429-485 of the human intestinal Npt2B protein defined by SEQ ID NO:1. The method may further include the step of observing a decrease or stabilization of the serum phosphate concentration. For example, the serum phosphate concentrations before and after the antibody treatment can be measured and compared.

The methods disclosed here can be used to attenuate or prevent hyperphosphatemia. In some embodiments, the serum phosphate concentration is reduced to or maintained at a level of or lower than about 150%, 125%, 120%, 115%, 110%, or 105% of a maximum physiological serum phosphate concentration in the accepted normal range. In some embodiments, the serum phosphate concentration is reduced to or maintained at a level within the normal range. For a human subject, the maximum high-normal serum phosphate concentration is 5.0 mg/dl. In a preferred embodiment, the serum phosphate concentration is reduced to or maintained at 5.5 mg/dl or lower or 5.0 mg/dl or lower in a human subject.

Patients at risk of developing or that have developed hyperphosphatemia include, but are not limited to, patients with: vitamin D intoxication from excessive intake of vitamin D compounds; excessive phosphate intake such as excessive use of phosphate-containing laxatives or enemas; renal disease or insufficiency such as renal failure, either acute or chronic, as described herein; primary hypoparathyroidism; PTH resistance states such as syndromes of tubular resistance to PTH including the various types of pseudohypoparathyroidism (1a, 1b, 1c, and 2) or severe hypomagnesemia, which impairs PTH secretion and causes peripheral PTH resistance; and/or conditions in which intracellular phosphate shifts to the extracellular space, such as rhabdomyolysis, tumor lysis, insulin deficiency or acute acidosis.

In some embodiments, the methods of the present invention are applied to reduce phosphate absorption in a human or non-human subject that has a kidney disease, receives a vitamin D compound (e.g., 1α,25-dihydroxyvitamin $D_3$), or both.

The amino acid sequences of intestinal Npt2B from various species are known. For example, the amino acid sequences of the human intestinal Npt2B (SEQ ID NO:1), mouse intestinal Npt2B (SEQ ID NO:2), rat intestinal Npt2B (SEQ ID NO:3), and chicken intestinal Npt2B (SEQ ID NO:4) can be found at NCBI GenBank Accession numbers 095436, Q9 DBP0, Q91109, and AAQ90408, respectively. Intestinal Npt2B proteins show four conserved extracellular loops. For example, the sequence similarity in all loops among the four species provided above is high (loop 1: >76%, loop 2: >64%, loop3: >82.5% and loop 4: >87.5%) with the three mammalian sequences having a higher percentage of identity than with the chicken sequence. For the human intestinal Npt2B (SEQ ID NO:1), extracellular loops 1-4 are amino acids 122-135, 234-362, 429-485, and 547-552, respectively. For the mouse intestinal Npt2B (SEQ ID NO:2), extracellular loops 1-4 are 125-138, 188-361, 440-461, and 549-554, respectively. For the rat intestinal Npt2B (SEQ ID NO:3), extracellular loops 1-4 are 112-136, 235-363, 430-486, and 548-551, respectively. For the chicken intestinal Npt2B (SEQ ID NO:4), extracellular loops 1-4 are 109-133, 185-358, 427-482, and 544-551, respectively.

Preferably, an antibody that binds to an epitope within extracellular loop 2 or 3 of an intestinal Npt2B protein is used to practice the methods of the present invention. For example, an antibody that binds to an epitope within amino acids 234-362 of SEQ ID NO:1 (i.e. loop 2) or amino acids 429-485 of SEQ ID NO:1 (i.e. loop 3) is used. In this regard, the antibody may bind to at least 4, 5, 6, 7, or 8 consecutive amino acids within amino acids 234-362 or 429-485 of SEQ ID NO:1 and, optionally, has an affinity Kd of about $10^{-4}$ M, $10^{-5}$ M, $10^{-6}$ M, $10^{-7}$ M, $10^{-8}$ M, $10^{-9}$ M, or less. In some embodiments, antibodies that bind to an epitope within amino acids 245-340 of SEQ ID NO:1, amino acids 252-330 of SEQ ID NO:1, amino acids 445-480 of SEQ ID NO:1, or amino acids 455-474 of SEQ ID NO:1 are used to practice the present invention. In some embodiments, antibodies against an epitope within the following intestinal Npt2B loop 2 or 3 fragments are used to practice the present invention: amino acids peptide 252-259, 278-285, 297-304, 323-330, 455-462, and 467-474 of the human intestinal Npt2B (SEQ ID NO:1); fragments of the mouse intestinal Npt2B (SEQ ID NO:2) that correspond to the above human intestinal Npt2B fragments; fragments of the rat intestinal Npt2B (SEQ ID NO:3) that correspond to the above human intestinal Npt2B fragments; or fragments of the chicken intestinal Npt2B (SEQ ID NO:4) that correspond to the above human intestinal Npt2B fragments. In one embodiment, antibodies against an epitope within amino acids 323-330 or 455-462 of the human intestinal Npt2B protein (SEQ ID NO:1) or a corresponding fragment from the mouse, rat, or chicken intestinal Npt2B protein are used to practice the present invention.

Corresponding fragments can be readily identified by any alignment program familiar to one of ordinary skill in the art. For example, Gapped BLAST can be used as described in Altschul et al. (*Nucleic Acids Res.* 25, 3389-3402, 1997). Gapped BLAST is available at the NCBI website. When utilizing Gapped BLAST program, the default parameters of the program can be used.

It is well within the capability of one of ordinary skill in the art to make an anti-intestinal Npt2B antibody such as an IgY antibody or antibody that binds to an epitope within an extracellular loop of Npt2B. In some embodiments, the antibody employed in the method is derived from an egg (e.g., egg yolk), in particular from an avian egg such as a chicken egg. The method of Polson, A., M. B. von Wechmar and M. H. van Regenmortel, "Isolation of Viral IgY Antibodies from Yolks of Immunized Hens," Immunological Communications 9:475-493 (1980), incorporated herein by reference in its entirety, can be used to produce a preparation of egg-yolk antibodies. Laying hens can be inoculated with an intestinal Npt2B protein or an immunogenic fragment thereof from an extracellular loop. Preferably, a suitable adjuvant is administered in conjunction with the inoculation to enhance the immunization. An adjuvant useful for this purpose is a water-in-oil emulsion adjuvant such as complete Freund's adjuvant. The intestinal Npt2B protein or an immunogenic fragment thereof from an extracellular loop causes the hens to produce anti-intestinal Npt2B antibodies which are passively transferred into the egg yolk of eggs laid by the hens. Egg yolks or whole eggs containing the antibody can be collected and homogenized to form an emulsion. The resulting emulsion can be dried to form a powder containing the antibody. This powder can then be formulated in a manner appropriate for oral administration and then administered orally to a human or non-human animal subject. The preparation may be administered orally as a diet or food supplement.

Antibodies of any isotype class or subclass (e.g., IgY, IgG, IgM, IgD, IgA, IgE, IgG1, IgG2, IgG3, IgG4, IgA1 and IgA2) as well as fragments thereof (whether produced by enzymatic or chemical digestion of such antibodies) and preparation of such antibodies by synthetic means or by expression of gene sequences encoding such antibodies or fragments thereof are contemplated. In one embodiment of IgY, antibodies in the egg yolks of an avian animal (e.g., chickens, pheasants, ducks, turkeys, geese and the like) are used to practice the present invention (see e.g., U.S. Pat. Nos. 5,080,895, 5,989,584 and 6,213,930, each of which is herein incorporated by reference in its entirety). Commercially available egg antibody purification kits, such as EGGstract® IgY Purification Systems (Promega; Madison, Wis.) or Eggcellent® Chicken IgY Purification (Pierce Biotechnology, Inc.; Rockford, Ill.), can be used to purify the antibodies. Antibodies can also be purified based on their affinity for peptides or protein fragments using standard means for affinity purification. Alternatively, eggs, egg yolks or dried egg yolk powder containing the antibodies can be mixed with a food directly for oral consumption or easily introduced into a pill, tablet, or capsule. Genes encoding such antibodies can also be identified using such antibodies through well established molecular cloning or phage display techniques to give rise to whole or partial monoclonal forms of such antibodies which could be used alone or in combination.

Compositions containing anti-intestinal Npt2B antibodies according to the present invention may be dosed, e.g., once, twice or three times a day. Dosing may optionally be subdivided in a manner in which a portion of the prescribed dose is ingested prior to consumption of food or beverages, another portion is ingested together with food or beverages, and yet other portions are ingested close in time after ingestion of food or beverages. The active ingredients can be administered by the oral route as particles or powder sprinkled or distributed on, or in, food; or dissolved or suspended in beverages; or provided in pharmaceutical solid dosage forms, such as tablets, capsules, and powders, or in liquid dosage forms, such as elixirs, syrups, and suspensions. In some embodiments, the antibody is administered with food or close in time (i.e. within about one hour before or after) to the consumption of a food having dietary phosphate. In some embodiments, the antibody is administered concomitantly with a phosphate binder.

Exemplary pharmaceutical compositions according to the present invention comprise IgY and optionally egg components, or IgY and optionally egg yolk components, optionally with additional stabilizers or pharmaceutically acceptable carriers. Whole eggs, or egg yolks, or egg yolks from which lipids are partially or mostly removed may be emulsified, optionally mixed with an encapsulation compound or lyoprotectant, and subjected to spray-drying or freeze-drying to form a powder.

Yolk antibodies can be partially purified, e.g., to remove large quantities of lipid. See Camenisch C et al., FASEB J. 1999, 13:81-88; Akita E & Nakai S, J. Immunol. Methods 1993, 160:207-214, each of which is incorporated herein by reference as if set forth in its entirety; as well as U.S. Patent Publication No. 2004/0087522, incorporated herein by reference as if set forth in its entirety.

Capsules or tablets may contain a controlled-release formulation as may be provided in a dispersion of active compound in hydroxypropyl methylcellulose or related material known to alter the kinetics of release of the active agent. Solid dosage forms can be manufactured as sustained release products to provide for continuous release of medication over a period of hours using known pharmaceutical techniques. Compressed tablets can be sugar coated or film coated to mask any unpleasant taste and protect the tablet from the atmosphere, or enteric coated for selective disintegration in the gastrointestinal tract. Both the solid and liquid oral dosage forms can contain coloring and flavoring to increase patient acceptance.

Stabilizers are protective agents that maintain the binding activity of the antibody under denaturing conditions, such as heat or acid. The stabilizer does not inhibit interaction of the antibodies with the target antigen, so that the desired biological effect is also maintained. Exemplary stabilizers include egg white, albumin or saccharide compounds. Preferably, the saccharide compound is present at about 5% to 30% of whole egg liquid (by weight), and more preferably in the amount of 10% to 20% of the whole egg liquid (by weight). The antibody is mixed with a saccharide compound in a liquid suspension and the suspension is then dried to produce a solid that contains the protein and the saccharide. Saccharide compounds useful as stabilizers include monosaccharides, disaccharides, polysaccharides, alkylated monosaccharides, alkylated disaccharides, alkylated polysaccharides, monosaccharide alcohols and alkylated monosaccharide alcohols. Preferably, such saccharide compounds are composed of or based on monosaccharide units of 5 or 6 carbons. Monosaccharides are single sugar residues having the formula $(CH_2O)_n$ wherein n is 3 or more. Examples of monosaccharides include but are not limited to glucose, ribose, fructose, galactose, talose, arabinose, fucose, mannose, xylose and erythrose. Monosaccharides in all isomeric forms such as α-isomers, β-isomers, D-isomers and L-isomers have activity. Disaccharides are molecules with two monosaccharide residues joined together by a glycosidic bond. Examples of disaccharides that can be used in the present invention include but are not limited to trehalose, maltose, sucrose, lactose, maltose and lactulose. Polysaccharides are molecules with three or more monosaccharides linked together in linear, unbranched chains or branched chains. Starch, glycogen and cellulose are examples of polysaccharides having hundreds or even thousands of monosaccharide residues. Starch can contain either linear, unbranched chains (amylose) or highly branched chains (amylopectin). Glycogen contains branched chains and cellulose contains linear, unbranched chains. Alkylated monosaccharides, alkylated disaccharides and alkylated polysaccharides are monosaccharides, disaccharides and polysaccharides with at least one of the hydrogen groups substituted by an alkyl group. Monosaccharide alcohols are acyclic polyols that contain three or more hydroxyl groups. They can be formed by converting the ketone or aldehyde groups of the monosaccharides to hydroxyl groups. Examples of monosaccharide alcohols include but are not limited to glycerine, mannitol, sorbitol, xylitol, lactitol, isomalt, maltitol, and hydrogenated starch hydrolysates. Alkylated monosaccharide alcohols are monosaccharide alcohols with at least one of the hydrogen groups substituted by an alkyl group.

Antibodies can also be attached to a matrix (polymeric or non-polymeric) substrate for the purposes of enhancing the efficacy or stability of the antibodies and then administered.

The invention will be more fully understood upon consideration of the following non-limiting examples.

Example 1

Inhibition of Phosphate Transport by Anti-Intestinal Npt2B Antibodies

Materials and Methods
Animals:
Single Comb White Leghorn laying hens were used for antibody production (3 hens per peptide antigen). Each human intestinal Npt2B peptide antigen (see Table 1 below for sequence and FIG. 1 for location on the cotransporter protein) was prepared by conjugating peptide to bovine gamma globulin using standard glutaraldehyde procedure.

TABLE 1

The amino acid sequence of peptides used to produce egg antibodies. Amino acid sequences are based on predicted conserved regions of intestinal Npt2B among animal species. Regions of interest include hydrophilic surface in the extracellular loops 1-3.

| Arbitrary Peptide # (SEQ ID NO) | amino acid sequence (amino acid positions on SEQ ID NO: 1) | enzyme location |
|---|---|---|
| 11 (SEQ ID NO: 5) | LVGGKMAG (124-131) | ECL-1[1] |
| 12 (SEQ ID NO: 6) | FHFKNGED (252-259) | ECL-2 NEAR D-3 |
| 13 (SEQ ID NO: 7) | LKVITKPF (264-271) | ELC-2 NEAR D-3 |
| 14 (SEQ ID NO: 8) | LDKKVISQ (278-285) | ELC-2 TOP D-3, 4 |
| 15 (SEQ ID NO: 9) | SLVKIWCK (297-304) | ELC-2 TOP D-3, 4 |
| 16 (SEQ ID NO: 10) | TSPSLCWT (323-330) | ELC-2 NEAR D-4 |
| 17 (SEQ ID NO: 11) | YPLTLGSN (455-462) | ECL-3 NEAR D-6 |
| 18 (SEQ ID NO: 12) | TTAILAAL (467-474) | ECL-3 NEAR D-6 |
| 19 (SEQ ID NO: 13) | VQSSSVFT (430-437) | ECL-3 NEAR D-5 |
| 20 (SEQ ID NO: 14) | LIGIGVIT (443-450) | ECL-3 NEAR D-5 |

TABLE 1-continued

The amino acid sequence of peptides used to produce egg antibodies. Amino acid sequences are based on predicted conserved regions of intestinal Npt2B among animal species. Regions of interest include hydrophilic surface in the extracellular loops 1-3.

| Arbitrary Peptide # (SEQ ID NO) | amino acid sequence (amino acid positions on SEQ ID NO: 1) | enzyme location |
|---|---|---|
| 31 (SEQ ID NO: 15) | EVATHYLE (235-242) | ECL-2 NEAR D-3 |
| 32 (SEQ ID NO: 16) | GIQNWTMK (332-339) | ECL-2 NEAR D-4 |
| 33 (SEQ ID NO: 17) | FVNFHLPD (354-361) | ECL-2 NEAR D-4 |
| 34 (SEQ ID NO: 18) | SPGNALRS (476-483) | ECL-2 NEAR D-4 |
| 35 (SEQ ID NO: 19) | ENIAKCQH (345-352) | ECL-3 NEAR D-6 |

[1]ECL = extracellular loop. There are 8 transmembrane domains (D) to intestinal Npt2B and 4 extracellular loops (ECL). Near D means it is closest to that domain. T = Top which means it is equally spaced between the domains presented. See FIG. 1.

Conjugation Preparation:

While the procedure for conjugation of peptides to carrier proteins can vary considerably (a number of kits for conjugation can be obtained from Pierce Scientific), as well as the nature of the carrier proteins, the method used in the studies described in this example involved the use of the glutaraldehyde procedure for conjugation of the desired peptide to the carrier protein bovine gamma globulin (BgG). BgG (4 mg) in 0.8 ml of 0.1 M sodium acetate buffer (pH=7) was mixed with 4 mg of the desired peptide. 0.52 ml of 0.02 M glutaraldehyde (in 0.1 M sodium acetate buffer) was added dropwise (to avoid foaming) to the peptide carrier protein mixture. The mixture was stirred for 2 hours. 20 mg glycine was then added to stop the reaction. The mixture was allowed to set for 1 hour and then was dialyzed against phosphate buffered saline (pH=7) overnight (MW=6000-8000). The dialyzed conjugate was then frozen at −80° C. until used.

Vaccine Preparation and Use:

To prepare a vaccine for each hen 0.5 mg of conjugate was diluted to a final concentration of 0.5 ml PBS and mixed with 0.5 ml of Freund's complete adjuvant (first injection) or incomplete adjuvant (booster vaccination) to form a water in oil emulsification capable of holding a bead when dripped on ice water. The hen was then injected in four sites (each leg and each breast) with 0.25 ml of the vaccine emulsion intramuscularly. The booster injection in incomplete adjuvant occurred 7 days later. Each peptide shown in Table 1 was separately conjugated to BgG and injected into 3 laying hens.

Antibody Sample Preparation:

Peak antibodies were achieved by 21 days, hence eggs were collected from day 21 to day 110. In approximately 30 day lots, egg yolks from each hen were separated from whole eggs, mixed and lyophilized. A sample of eggs from each hen were collected, yolks were separated and IgY was polyethylene purified using procedures described in Polson et al., Immunol. Commun. 1980, 9:475-493). Antibodies prepared using this method were frozen (−20° C.) and served as reagents for cell culture and in vitro enzyme assay.

Cells:

Caco-2 cells were obtained from ATCC (#HTB-37, ATCC). Caco-2 cell line is a colorectal adenocarcinoma cell line and was used to model intestinal enterocytes in this study.

Phosphate Uptake Assay:

Medium from a sub-confluent monolayer of Caco-2 cells was removed and cells were washed with a buffer A (137 mM NaCl, 5.4 mM KCl, 2.8 mM $CaCl_2$, 1.2 mM $MgSO_4$, 14 mM Tris-HCl pH 7.4=sodium buffer) or with a buffer B (137 mM choline chloride, 5.4 mM KCl, 2.8 mM $CaCl_2$, 1.2 mM $MgSO_4$, 14 mM Tris-HCl pH 7.4=sodium free buffer). One ml of buffer A or B containing the antibody at 0.1 mg/ml was added to the cells and incubated for 1 hour at 37° C. After one hour incubation, buffer A or buffer B was aspirated and 100 µl of buffer A or buffer B containing $K_2H^{32}PO_4$ (1 µCi/mL) was added. Cells were incubated for another 20 min at 37° C. During the incubation period, the plate was shaken continuously at 100 rpm/minute. Phosphate uptake was terminated by removing the uptake buffers and by washing the cells with an ice-cold stop solution (14 mM Tris-HCl pH 7.4 and 137 mM choline chloride). Cells were lysed and collected using a 1% solution of Triton X-100. Aliquots were added to scintillation fluid and radioactivity was determined by liquid scintillation counting. The difference in radioactivity recovered between the assays, using the two buffers (buffer A and buffer B), represents the sodium dependent transport of phosphate.

Results

Figure 2:
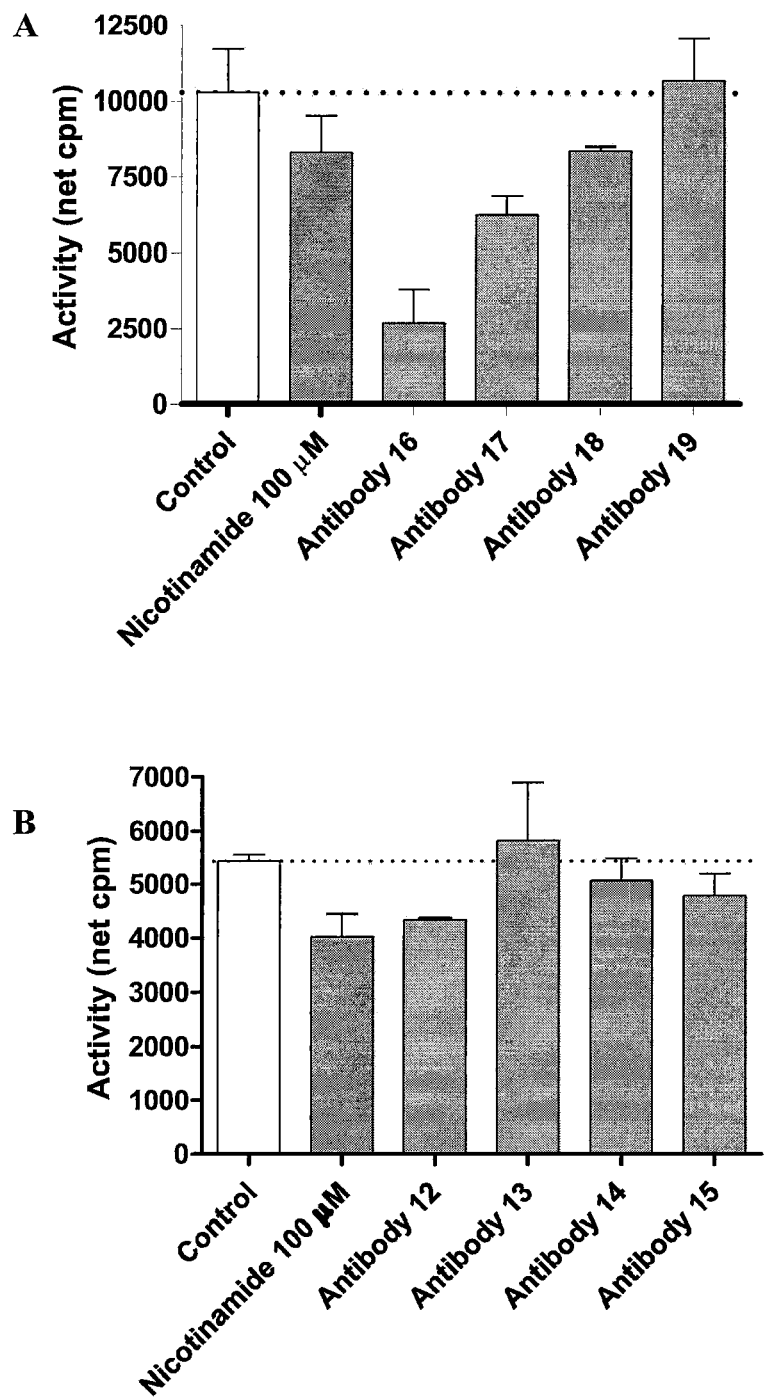
FIG. 2 shows the effects of nicotinamide (positive control in inhibiting phosphorous uptake) and various anti-intestinal Npt2B peptide antibodies on phosphorous uptake by Caco-2 cells in vitro. From left to right treatments are: 2A, control (antibody from adjuvant injected hens), nicotinamide, and anti-peptide antibodies (PEG purified from egg yolk) 16, 17, 18, and 19; 2B, control, nicotinamide, and anti-peptide antibodies (PEG purified from egg yolk) 12, 13, 14, and 15.

As shown in FIG. 2 with Caco-2 cells, antibodies to peptides 12, 14, 15, 16, 17, and 18 inhibited phosphate transport. The relative effectiveness of inhibition was 16>17>18>12>15=14. Antibodies to peptide 16 and peptide 17 were more effective than nicotinamide (positive control for inhibiting phosphorous uptake) in inhibiting phosphate transport.

Example 2

Effect of Anti-Intestinal Npt2B Antibodies on Body Weight Gain, Plasma Phosphate Concentration, and Excreta Phosphate Materials and Methods The production of anti-human intestinal Npt2B antibodies using various Npt2B peptides has been described in Example 1 above. Instead of purified IgY antibodies, dried yolk powder containing the antibodies was used directly in the feeding study presented in this example.

Male one-day old single comb white leghorn chicks (2 pens of five chicks) were assigned to either a control diet or an antibody diet (1 g/kg diet of freeze dried egg yolk antibody) to one of the 14 peptides of Npt2B (peptides 11-20 and 31-34 in Table 1). The control diet is a standard nutrient adequate corn-soybean meal based diet and contained 1 g/kg diet of adjuvant injected control dried egg yolk powder. The antibody diet is the same as the control diet except the peptide specific antibody powder replaced the control powder. Chicks were fed the diets for 21 days. Then, body weights were determined, blood samples were collected for determining total plasma phosphorous level using a Roche/Hitachi analyzer (based on the reaction of phosphate with ammonium molybdate to form ammonium phosphomolybdate without reduction), and excreta sample for the last 3 days on the diets were collected for each pen and analyzed for total phosphorous (dry weight basis).

Results

As shown in Table 2, anti-peptides 11, 13, 15-17, 20, 31, and 32 suppressed body weight gain; anti-peptides 20, 32, and 34 decreased the plasma phosphate levels; and anti-peptides 11, 12, 14, 17-20, and 32 increased excreta phosphorous.

TABLE 2

The effect of feeding egg antibody (1 g/kg diet) to select peptides of the intestinal Npt2B on body weight gain, plasma phosphorous concentration, and excreta phosphorous.[1]

| treatment | Body weight gain (g)[2] | Blood phosphate (mg/dL)[3] | Excreta phosphate (%)[4] | Mean excreta phosphate[4] |
|---|---|---|---|---|
| control | 183 ± 8.4 | 6.6 ± 0.5 | 1.24, 1.26 | 1.25 |
| anti-peptide 11 | 164 ± 6.1[6] | 6.6 ± 0.2 | 1.3, 1.44 | 1.37 |
| anti-peptide 12 | 180 ± 5.9 | 6.2 ± 0.4 | 1.38, 1.46 | 1.42 |
| anti-peptide 13 | 166 ± 10[7] | 6.3 ± 0.4 | 1.16, 1.34 | 1.25 |
| anti-peptide 14 | 175 ± 3.9 | 6.6 ± 0.2 | 1.42, 1.22 | 1.32 |
| anti-peptide 15 | 170 ± 8.6[7] | 6.7 ± 0.4 | 1.38, 1.18 | 1.28 |
| anti-peptide 16 | 145 ± 14[5] | 6.7 ± 0.3 | 1.02, 1.22 | 1.12 |
| anti-peptide 17 | 165 ± 7.5[6] | 6.3 ± 0.1 | 1.32, 1.5 | 1.41 |
| anti-peptide 18 | 178 ± 6.2 | 6.6 ± 0.1 | 1.7, 1.2 | 1.45 |
| anti-peptide 19 | 176 ± 8.0 | 6.4 ± 0.3 | 1.32, 1.34 | 1.33 |
| anti-peptide 20 | 170 ± 10[7] | 6.0 ± 0.2[9] | 1.36, 1.5 | 1.43 |
| anti-peptide 31 | 169 ± 7.0[7] | 6.3 ± 0.2 | 1.16, 1.12 | 1.14 |
| anti-peptide 32 | 163 ± 9.2[5] | 5.7 ± 0.3[8] | 1.28, 1.4 | 1.34 |
| anti-peptide 33 | 177 ± 9.5 | 6.6 ± 0.2 | 1.14, 1.18 | 1.16 |
| anti-peptide 34 | 182 ± 5.2 | 6.0 ± 0.2[10] | 1.22, 1.24 | 1.23 |

[1]Two pens of five one-day old Single Comb White Leghorn male chicks were fed a nutrient adequate (UW-Standard poultry chick starter diet) with control egg yolk powder (1 g/kg diet of dried egg yolk from hens injected with adjuvants alone) or the egg yolk powder (1 g/kg diet) of hens immunized with the peptide antigens indicated. Chicks were raised for 3 weeks and body weight gain during this period (less starting weight) was measured. At 21 days of age, all chicks were blood sampled, plasma was collected and analyzed for phosphorous. All excreta was collected from the manure pan below each pen of chicks over the last 3 days of the study was collected and analyzed for total phosphorous.
[2]Gain ± standard error = 21 day weight less starting weight.
[3]Plasma phosphorous ± standard error.
[4]Two pens were sampled and analyzed. The raw values (% of dry matter) and mean are shown. 6*, 5, 7* Indicate $p < 0.05$**, $p < 0.07$*, and $p < 0.1$*** relative to the control.
[5]$p < 0.05$;
[6]$p < 0.07$;
[7]$p < 0.1$;
[8]$p = 0.07$;
[9]$p = 0.13$; and
[10]$p = 0.16$.

Example 3

Effect of Anti-Intestinal Npt2B Antibodies on Body Weight Gain, Plasma Phosphate Concentration, And Bone Ash Materials and Methods The production of anti-human intestinal Npt2B antibodies using peptide 16 has been described in Example 1 above. Instead of purified IgY antibodies, dried yolk powder containing the antibodies was used directly in the feeding study presented in this example.

Seven-day old broiler chicks were assigned to either a control diet (4 pens of 5 broiler chicks) or an antibody diet (1 g/kg diet of freeze dried egg yolk antibody) (8 pens of 5 broiler chicks). The control diet is a standard nutrient adequate diet and contained 1 g/kg diet of adjuvant injected control dried egg yolk powder. The antibody diet is the same as the control diet except the anti-peptide 16 antibody powder replaced the control powder. Diets began when chicks were 7 days of age and fed until 21 days of age. Body weights were determined at day 14 and day 21. At day 21, blood samples were collected for determining total plasma phosphorous level using a Roche/Hitachi analyzer (based on the reaction of phosphate with ammonium molybdate to form ammonium phosphomolybdate without reduction), and the right tibia was harvest for determination of fat free dried bone ash (ether extracted, dried, and ashed in a muffle furnace and the ratio of ash/dry fat-free bone determined and converted to %).

Results

As shown in Table 3, broilers fed antibody to peptide 16 reduced 14 day body weight gain compared to broilers fed the adjuvant control antibody yolk powder (413 g vs. 495 g for anti-peptide 16 diet group and control diet group, respectively, p=0.08). Plasma phosphorous did not differ between these two treatment groups (6.12 mg/dl vs 6.14 mg/dl for anti-peptide 16 diet group and control diet group, respectively). Broilers fed antibody to peptide 16 reduced bone mineral content compared to broilers fed the adjuvant control antibody yolk powder (0.524% vs. 0.539% for anti-peptide 16 diet group and control diet group, respectively). Broilers are a very rapid growing strain relative to the leghorn. Body weight during the first 3 weeks in broilers increases from 35 grams to approximately 500-600 grams (more than a 15 fold increase), whereas in leghorn the increase is from 35 g to only about 180 g (5-6 fold increase). Hence, body weight gain in the broiler can be a sensitive indicator to dietary available phosphorous. From the bone ash data, the priority for maintaining blood phosphate is higher in this breed than making bone and growing muscle. This supports growth being the most sensitive indicator in this strain.

TABLE 3

The effect of feeding egg antibody (1 g/kg diet) to peptide 16 of intestinal Npt2B on body weight gain, plasma phosphorous concentration, and bone ash.

| | Control | Anti-peptide 16 |
|---|---|---|
| Body weight gain (g) | 495 ± 15* | 413 ± 16* |
| Plasma phosphate (mg/dL) | 6.14 ± 0.31 | 6.12 ± 0.19 |
| Bone ash (%) | 0.539 ± 0.005** | 0.524 ± 0.005** |

*Broilers fed antibody to peptide 16 reduced 14 day body weight gain compared to broilers fed the adjuvant control antibody yolk powder (p = 0.0003).
**Broilers fed antibody to peptide 16 reduced bone mineral content compared to broilers fed the adjuvant control antibody yolk powder (p = 0.02).

Example 4

Orally Administered Antibody Can Reach and Block the Activity of an Intestinal Brush Border Membrane-Associated Protein Materials and Methods Antibody Preparation:

Single Comb White Leghorn laying hens were used for antibody production (3 hens per peptide antigen). Chicken intestinal alkaline phosphatase was purchased from Worthington. To prepare a vaccine for each hen 0.5 mg of chicken intestinal alkaline phosphatase was diluted to a final concentration of 0.5 ml PBS and mixed with 0.5 ml of Freund's complete adjuvant (first injection) or incomplete adjuvant (booster vaccination) to form a water in oil emulsification capable of holding a bead when dripped on ice water. The hen was then injected in four sites (each leg and each breast) with 0.25 ml of the vaccine emulsion intramuscularly. The booster injection in incomplete adjuvant occurred 7 days later.

Peak antibodies were achieved by 21 days, hence eggs were collected from day 21 to day 110. In approximately 30 day lots, egg yolks from each hen were separated from whole eggs, mixed and lyophilized. Dried egg yolk powder containing the antibody was stored at room temperature until use in animal feeding studies.

Animal Experiment:

The chicken model used in this study was described by Biehl and Baker, J. Nutr. 1997, 127:2054-2059 with the exception of antibodies to intestinal alkaline phosphatas. The negative control used in this study was a Pi deficient diet (Pi=inorganic phosphate which are largely mineral phosphates or phosphate from animal tissues and products such as milk and eggs), where the dietary phosphorous used was phytic phosphate. As shown in the results below, this dietary treatment resulted in low plasma phosphorous. The positive control was the same diet as the negative control, but supplemented with 1α-hydroxyvitamin $D_3$ (20 µg/kg diet, Sigma). As shown in the results below, this dietary treatment increased blood phosphorous levels in comparison to the negative control. All the remaining dietary treatments were the positive control plus the antibody (1 g of dried egg yolk powder produced as described above). The negative and positive controls were fed 1 g/kg diet of dried yolk powder from hens injected with the adjuvant. These egg yolk powders lacked specific antibodies.

A total of 3 treatments were used (negative control, positive control, positive control plus anti-chicken intestinal alkaline phosphatase antibodies). Six one-day old male Single Comb White Leghorn chicks were assigned to each of the dietary treatments. Chicks were fed the dietary treatments for 10 days, weighed, then blood sampled for determining plasma phosphorous concentration using a Roche/Hitachi analyzer (based on the reaction of phosphate with ammonium molybdate to form ammonium phosphomolybdate without reduction).

Results

Antibodies to chicken intestinal alkaline phosphatase were effective at reducing plasma phosphorous levels (Table 4).

TABLE 4

Plasma phosphorous of chickens fed anti-intestinal alkaline phosphatases (IAP) in the presence of active vitamin $D^1$

| Dietary treatment | Plasma phosphate (mg/dL) | Standard error |
|---|---|---|
| Pi Deficient | 3.92 | 0.35 |
| Active vitamin $D^2$ | 6.70 | 0.51 |
| Chicken IAP** | 4.73 | 0.29 |

[1] One day old leghorn chicks (n = 6) were fed a Pi deficient diet containing phytic phosphorous with the addition of 1α-hydroxyvitamin $D_3$ alone (active vitamin D, 20 µg/kg diet) or the addition of 1α-hydroxyvitamin $D_3$ plus an egg antibody (1 g/kg diet of dried egg yolk antibody powder) to chicken intestinal alkaline phosphatase. Plasma phosphorous was measured after 10 days of feeding the diet.
[2] Chickens on the active vitamin D diet (1α-hydroxyvitamin $D_3$) had increased plasma phosphorous relative to the chickens on Pi deficient diet (p = 0.0004).
**Chicks fed the active vitamin D diet (1α-hydroxyvitamin $D_3$) supplemented with antibody to chicken intestinal alkaline phosphatase had reduced plasma phosphorous relative to active vitamin D alone treatment at p < 0.05.

Example 5

Reducing Serum Phosphate Level in Adenine-Induced Uremic Animals

The animal model used in this example is the adenine-induced uremic rat model (see e.g., Yokazawa et al., Nephron 1986, 44:230-234; Katsumata et al., Kid Intl 2003, 64:441-450; and Levi R et al., J Am Soc Nephrol 2006, 17:107-112, each of which is herein incorporated by reference in its entirety).

Rats (e.g., male Sprague Dawley rats approximately 175-250 g, up to 10 rats per group) are fed a control diet or a uremia-inducing adenine diet (e.g., containing 0.75% adenine) for a period of weeks (e.g., 3 to 5 weeks or longer). Rats fed the adenine diet will develop hyperphosphatemia with level of serum phosphate higher than 4.4 mmol/L. These rats will also develop vitamin $D_3$, (1α-hydroxyvitamin $D_3$ and 1α,25-dihydroxyvitamin $D_3$) deficiency. The daily oral treatment of these rats fed the adenine diet with increasing amount of anti-intestinal Npt2B antibody such as those described in Example 1 will result in a dose dependent reduction of serum phosphate levels. If these antibodies are given within the first 4 weeks of adenine treatment and thereafter, these anti-intestinal Npt2B antibodies will prevent, delay or reverse the development of hyperphosphatemia in these rats.

In other groups, rats fed the adenine diet are given a form of vitamin D (e.g., 25-hydroxyvitamin D or derivatives thereof or an active vitamin D agent such as 1α,25-dihydroxyvitamin $D_3$) to prevent or correct active vitamin D deficiency. This treatment will make rats more susceptible to hyperphosphatemia and will exacerbate hyperphosphatemia in these rats once developed. Treating these rats receiving vitamin D (e.g., 1α,25-dihydroxyvitamin $D_3$) orally with increasing dose of anti-intestinal Npt2B antibody such as those described in Example 1 will reduce serum phosphate levels in these rats in a dose dependent manner. If the antibodies are given within the first 4 weeks of adenine treatment and thereafter, these anti-intestinal Npt2B antibodies will prevent or delay the development or exacerbation of hyperphosphatemia.

Similar experiments can be conducted using other adenine-induced uremic animals such as dogs, pigs, and monkeys.

Example 6

Reducing Serum Phosphate Level in 5/6 Nephrectomized Rats

For 5/6 nephrectomy (see e.g., Cozzolino M et al., Kidney Int. 2003, 64:1653-61), several branches of the left renal artery were ligated and the right kidney excised. 5/6 nephrectomized rats (e.g., male Sprague Dawley rats, approximately 175-250 g, up to 10 rats per group) are fed a high phosphate diet (e.g., 0.9% phosphate). These rats will become uremic weeks after surgery (e.g., 4 to 8 weeks) and develop renal failure, hyperphosphatemia, and active vitamin $D_3$ (1α-hydroxyvitamin $D_3$ and 1α,25-dihydroxyvitamin $D_3$) deficiency. The daily oral treatment of these 5/6 nephrectomized rats fed the high phosphate diet with increasing amount of anti-intestinal Npt2B antibody such as those described in Example 1 will reduce the serum phosphate level in a dose dependent manner in these rats. If the antibodies such as those described in Example 1 are given within the first few weeks following surgery and thereafter they will either prevent or delay the development of hyperphosphatemia in these rats.

In other groups, 5/6 nephrectomized rats fed the high phosphate diet are given a form of vitamin D (e.g., 25-hydroxyvitamin D or derivatives thereof or an active vitamin D agent such as 1α,25-dihydroxyvitamin $D_3$) to prevent or correct active vitamin D deficiency. However, this treatment will make rats more susceptible to hyperphosphatemia and will exacerbate hyperphosphatemia in these rats once developed. Treating these rats receiving vitamin D (e.g., 1α,25-dihydroxyvitamin $D_3$) orally with increasing dose of anti-intestinal Npt2B antibody such as those described in Example 1 will reduce the serum phosphate level. If the antibodies are given within the first few weeks of surgery and thereafter, these anti-intestinal Npt2B antibodies will prevent or delay the development or exacerbation of hyperphosphatemia in these rats.

The present invention is not intended to be limited to the foregoing examples, but to encompass all such modifications and variations as come within the scope of the appended claims.

We claim:

1. A method of reducing phosphate absorption in a human or non-human animal subject at risk of developing or having developed hyperphosphatemia, the method comprising the step of: administering orally to the subject an IgY anti-intestinal sodium phosphate cotransporter type 2B (Npt2B) antibody that binds to Npt2B of SEQ ID NO:1 in an amount effective to reduce or maintain the serum phosphate concentration in the subject at a level of or lower than 150% of a maximum physiological serum phosphate concentration of 5.5 mg/dl.

2. The method of claim 1, wherein the subject is a human subject.

3. The method of claim 1, wherein the subject has a kidney disease.

4. The method of claim 3, wherein the kidney disease is selected from end stage renal disease, acute renal failure, chronic renal failure, polycystic kidney disease, chronic kidney disease, acute tubular necrosis, an infection that reduces kidney function, and a urinary tract obstruction.

5. The method of claim 1, wherein the subject is receiving a vitamin D compound.

6. The method of claim 1, wherein the antibody is obtained from an avian egg.

7. The method of claim 1, wherein the antibody is administered with a phosphate binder.

8. The method of claim 1, further comprising the steps of measuring the serum phosphate concentration after the anti-intestinal Npt2B antibody is administered and comparing the concentration to that before the anti-intestinal Npt2B antibody is administered.

9. A method of reducing phosphate absorption in a human or non-human animal subject at risk of developing or having developed hyperphosphatemia, the method comprising the step of: administering orally to the subject an anti-intestinal sodium phosphate cotransporter type 2B (Npt2B) antibody that binds to an epitope within amino acids 234-362 of SEQ ID NO:1 in an amount effective to reduce or maintain the serum phosphate concentration in the subject at a level of or lower than 150% of a maximum physiological serum phosphate concentration of 5.5 mg/dl.

10. The method of claim 9, wherein the anti-intestinal Npt2B antibody binds to an epitope within amino acids 245-340 of SEQ ID NO:1.

11. The method of claim 9, wherein the anti-intestinal Npt2B antibody binds to an epitope within amino acids 252-330 of SEQ ID NO:1.

12. The method of claim 9, wherein the subject is a human subject.

13. The method of claim 9, wherein the subject has a kidney disease.

14. The method of claim 13, wherein the kidney disease is selected from end stage renal disease, acute renal failure, chronic renal failure, polycystic kidney disease, chronic kidney disease, acute tubular necrosis, an infection that reduces kidney function, and a urinary tract obstruction.

15. The method of claim 9, wherein the subject is receiving a vitamin D compound.

16. The method of claim 9, wherein the antibody is an IgY antibody.

17. The method of claim 9, wherein the antibody is administered with a phosphate binder.

18. The method of claim 9, further comprising the steps of measuring the serum phosphate concentration after the anti-intestinal Npt2B antibody is administered and comparing the concentration to that before the anti-intestinal Npt2B antibody is administered.

19. A method of reducing phosphate absorption in a human or non-human animal subject at risk of developing or having developed hyperphosphatemia, the method comprising the step of: administering orally to the subject an anti-intestinal sodium phosphate cotransporter type 2B (Npt2B) antibody that binds to an epitope within amino acids 429-485 of SEQ ID NO:1 in an amount effective to reduce or maintain the serum phosphate concentration in the subject at a level of or lower than 150% of a maximum physiological serum phosphate concentration of 5.5 mg/dl.

20. The method of claim 19, wherein the anti-intestinal Npt2B antibody binds to an epitope within amino acids 445-480 of SEQ ID NO:1.

21. The method of claim 19, wherein the anti-intestinal Npt2B antibody binds to an epitope within amino acids 455-474 of SEQ ID NO:1.

22. The method of claim 19, wherein the subject is a human subject.

23. The method of claim 19, wherein the subject has a kidney disease.

24. The method of claim 23, wherein the kidney disease is selected from end stage renal disease, acute renal failure, chronic renal failure, polycystic kidney disease, chronic kidney disease, acute tubular necrosis, an infection that reduces kidney function, and a urinary tract obstruction.

25. The method of claim 19, wherein the subject is receiving a vitamin D compound.

26. The method of claim 19, wherein the antibody is an IgY antibody.

27. The method of claim 19, wherein the antibody is administered with a phosphate binder.

28. The method of claim 19, further comprising the steps of measuring the serum phosphate concentration after the anti-intestinal Npt2B antibody is administered and comparing the concentration to that before the anti-intestinal Npt2B antibody is administered.

29. A method of reducing side effects of vitamin D therapy in a human subject comprising the step of: administering orally to the subject (a) a vitamin D compound and (b) an anti-intestinal sodium phosphate cotransporter type 2B (Npt2B) antibody that binds to Npt2B of SEQ ID NO: 1 in an amount effective to reduce hyperphosphatemia induced by vitamin D therapy, to maintain the serum phosphate concentration in the subject at a level of or lower than 150% of a maximum physiological serum phosphate concentration of 5.5 mg/dl.

30. The method of claim 29, wherein the subject has a kidney disease.

31. The method of claim 29, wherein the subject has a vitamin D deficiency.

32. The method of claim 29, wherein the antibody is administered with a phosphate binder.

33. The method of claim 29, further comprising the steps of measuring the serum phosphate concentration after the anti-intestinal Npt2B antibody is administered and comparing the concentration to that before the anti-intestinal Npt2B antibody is administered.

* * * * *